US009846119B2

(12) United States Patent
Kubo

(10) Patent No.: US 9,846,119 B2
(45) Date of Patent: Dec. 19, 2017

(54) INFORMATION PROCESSING APPARATUS, MEASUREMENT SYSTEM, INFORMATION PROCESSING METHOD, AND STORAGE MEDIUM FOR DETERMINING AT LEAST ONE MEASUREMENT CONDITION TO MEASURE REFLECTION CHARACTERISTICS OF AN OBJECT WHICH IS TO BE USED TO GENERATE A VIRTUAL IMAGE

(71) Applicant: CANON KABUSHIKI KAISHA, Tokyo (JP)

(72) Inventor: Hiroyuki Kubo, Ikoma (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/671,903

(22) Filed: Mar. 27, 2015

(65) Prior Publication Data
US 2015/0276591 A1  Oct. 1, 2015

(30) Foreign Application Priority Data

Mar. 31, 2014 (JP) ................................ 2014-074568

(51) Int. Cl.
*G06T 11/00* (2006.01)
*G01N 21/47* (2006.01)
(52) U.S. Cl.
CPC ........ *G01N 21/4738* (2013.01); *G06T 11/001* (2013.01); *G01N 2201/061* (2013.01)
(58) Field of Classification Search
None
See application file for complete search history.

(56) References Cited

U.S. PATENT DOCUMENTS 6,268,863 B1 *  7/2001  Rioux .................... G06T 15/00
                                                           345/426
2004/0150643 A1 *  8/2004  Borshukov ........... G06T 7/0065
                                                           345/426

(Continued)

FOREIGN PATENT DOCUMENTS

JP      2002-500754 A     1/2002
JP      2007-26049 A      2/2007

*Primary Examiner* — Edward Martello
(74) *Attorney, Agent, or Firm* — Canon USA, Inc. I.P. Division

(57) ABSTRACT

A versatile method(s) capable of reducing the time required for measurement of reflection characteristics and the amount of data indicating measurement results is (are) provided herein. An information processing apparatus may determine a measurement condition to measure reflection characteristics of an object which is to be used to generate a virtual image that can be obtained when a virtual object is observed from a predetermined virtual viewpoint in a virtual space where a virtual light source and virtual object are disposed. The information processing apparatus may include a path acquisition unit configured to acquire a path of light along which light emitted from the virtual light source reaches the virtual viewpoint after being reflected on the virtual object, and a determination unit configured to determine a measurement condition of the reflection characteristics corresponding to the path of light based on the path of light acquired by the path acquisition unit.

16 Claims, 15 Drawing Sheets

(56) References Cited

U.S. PATENT DOCUMENTS

2005/0068537 A1* 3/2005 Han .................. G01N 21/4795
356/446
2010/0053153 A1* 3/2010 Baril ....................... G06T 9/001
345/419

* cited by examiner

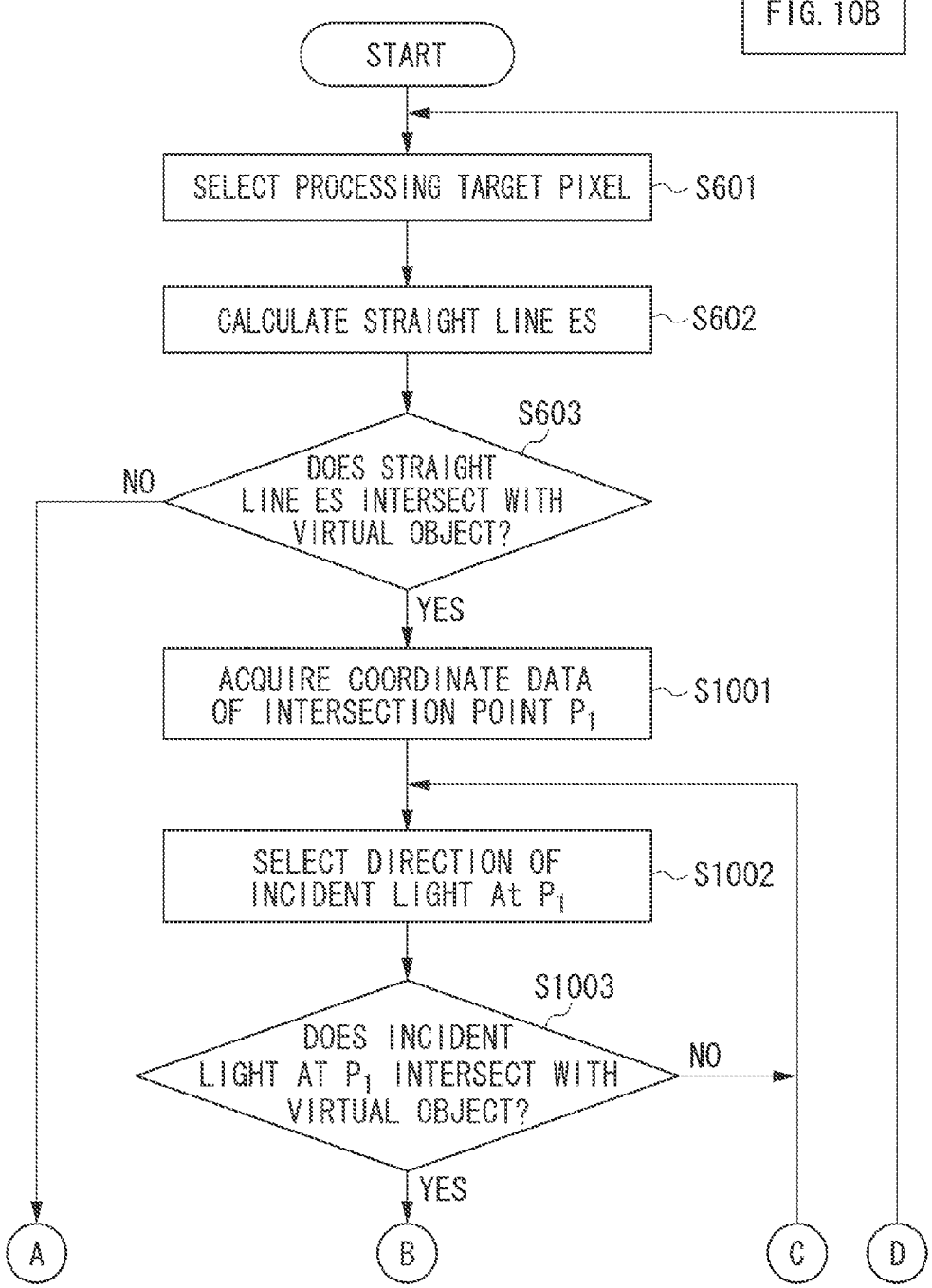

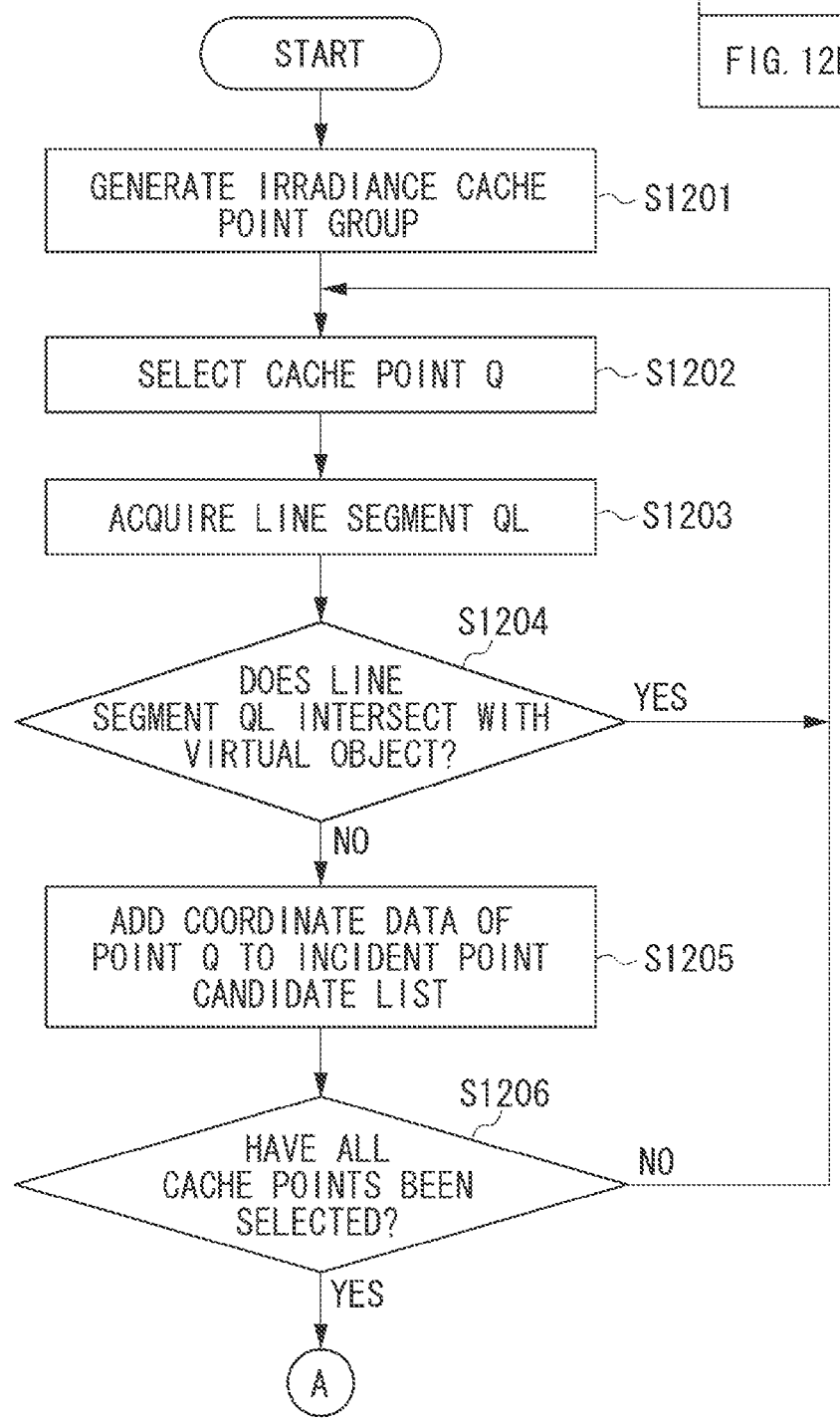

INFORMATION PROCESSING APPARATUS, MEASUREMENT SYSTEM, INFORMATION PROCESSING METHOD, AND STORAGE MEDIUM FOR DETERMINING AT LEAST ONE MEASUREMENT CONDITION TO MEASURE REFLECTION CHARACTERISTICS OF AN OBJECT WHICH IS TO BE USED TO GENERATE A VIRTUAL IMAGE

BACKGROUND OF THE INVENTION

Field of the Invention

The present inventions relate to a measurement of reflection characteristics.

Description of the Related Art

A computer graphics (CG) based technique capable of generating an image that accurately reproduces the texture of a real object is conventionally known. To generate a CG image of an object in a virtual space that reflects the texture of an actually existing object, it is necessary to perform rendering processing based on measurement results of reflection characteristics of a target real object. A bidirectional reflectance distribution function (BRDF) is an exemplary function that can represent reflection characteristics of an opaque object (e.g., a metal). A bidirectional scattering surface reflectance distribution function (BSSRDF) is an exemplary function that can represent reflection characteristics of a semitransparent object (e.g., a human skin or a marble) into which incident light can enter and cause scattering. Each of these reflection characteristic functions is a multivariable function, which takes a long time to perform a fine measurement for respective variables (e.g., incident light direction and outgoing light direction). For example, in many cases, BRDF data of a metal surface reveals that the peak width is less than 1 [deg] and the luster is sharp, although it depends on the type and surface finishing of each metal. To measure a metal that is sharp in luster, it is necessary to perform a BRDF measurement with sufficiently reduced sampling width. If the BRDF measurement is performed at intervals of 1 [deg] for each of the incident light direction and the outgoing light direction, the number of times of measurement rises up to approximately 350,000,000. Such a large-scale measurement is unrealistic when the time actually required to finish the entire measurement is taken into consideration. Further, the amount of measurement data to be processed becomes huge.

In view of the above, a method for reducing the time required for the reflection characteristic measurement or a method for reducing a required storage area are conventionally proposed. As discussed in Japanese Unexamined Patent Application Publication (Translation of PCT Application) No. 2002-500754, using a charge-coupled device (CCD) line camera is conventionally proposed to reduce the reflection characteristic measurement time because reflectance values can be simultaneously acquired in many outgoing directions. Further, as discussed in Japanese Patent Application Laid-Open No. 2007-26049, there is a conventional technique that restricts a reflection characteristic measurement target to fabric materials in such a way as to limit the incidence direction and the outgoing direction to be measured, so that the acquisition of reflection characteristics can be realized by a smaller number of times of measurement.

However, according to the technique discussed in Japanese Unexamined Patent Application Publication (Translation of PCT Application) No. 2002-500754, it is unfeasible to sufficiently reduce the number of times of measurement for the thoroughly performed BRDF measurement because there is a limit to camera density of the line camera and the simultaneous measurement can be performed only along a line. Further, the technique discussed in Japanese Patent Application Laid-Open No. 2007-26049 is dissatisfactory in versatility to the material type because measurement target materials are limited in type, although the number of times of measurement or the storage area can be reduced to a certain extent.

SUMMARY OF THE INVENTION

A versatile method(s) capable of reducing the time required for measurement of reflection characteristics and the amount of data indicating measurement results is(are) provided herein.

According to an aspect of one or more embodiments discussed herein, at least one information processing apparatus determines at least one measurement condition to measure reflection characteristics of an object which is to be used to generate a virtual image that can be obtained when a virtual object is observed from a predetermined virtual viewpoint in a virtual space in which a virtual light source and a virtual object are disposed. The at least one information processing apparatus may include an information acquisition unit configured to acquire information indicating a positional relationship between the virtual light source, the virtual object, and the virtual viewpoint in the virtual space and information indicating a shape of a surface of the virtual object on which light emitted from the virtual light source is incident; and a determination unit configured to determine at least one measurement condition of measurement conditions that can be used for a reflection characteristic measurement as at least one measurement condition to be used in the reflection characteristic measurement, based on the information indicating the positional relationship and the information indicating the shape acquired by the information acquisition unit. At least one information processing apparatus may include a path acquisition unit configured to acquire a path of light along which light emitted from the virtual light source reaches the virtual viewpoint after being reflected on the virtual object, based on the information indicating the positional relationship and the information indicating the shape. In one or more embodiments of the at least one information processing apparatus, the determination unit may determine a reflection characteristic measurement condition that corresponds to the path of light, based on the path of light acquired by the path acquisition unit.

According to other aspects of the present inventions, one or more information processing apparatus, one or more measurement system, one or more information processing method, and one or more storage medium are discussed herein. Further features of the present inventions will become apparent from the following description of exemplary embodiments with reference to the attached drawings.

DESCRIPTION OF THE EMBODIMENTS

A measurement system according to a first exemplary embodiment measures reflection characteristics of a real object to generate a CG image of a virtual object (i.e., an object in a virtual space) that reflects the texture of an actually existing object (i.e. the real object), as described in detail below. The measurement system according to the present exemplary embodiment measures only reflection characteristics required when a CG image is generated in such a manner that the virtual object is observed from a specific viewpoint, in a virtual space in which a virtual object and a virtual light source are present. Therefore, the measurement system according to the present exemplary embodiment can obtain an intended CG image without thoroughly performing the measurement of reflection characteristics based on all conditions. Therefore, the measurement system according to the present exemplary embodiment can reduce the time and data amount required in the reflection characteristic measurement.

Figure 1:
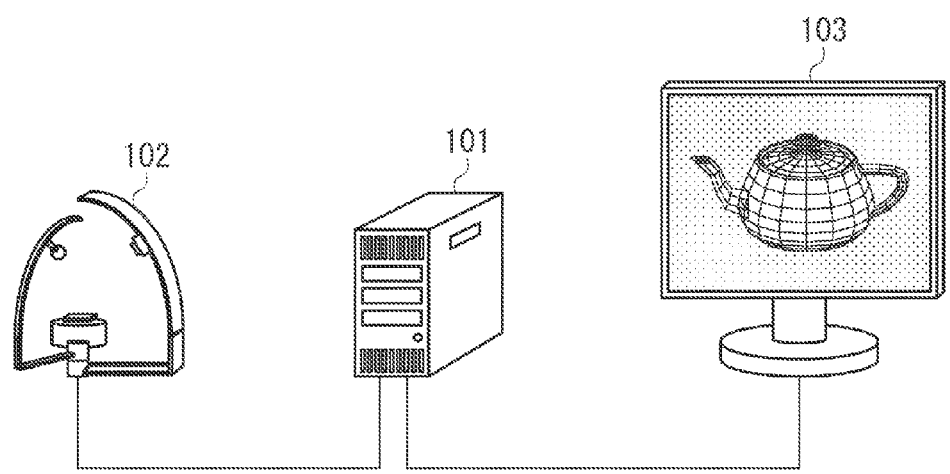
FIG. 1 illustrates a configuration example of a reflection characteristic measurement system.

FIG. 1 illustrates a configuration example of a reflection characteristic measurement system according to the present exemplary embodiment. The reflection characteristic measurement system illustrated in FIG. 1 includes an information processing apparatus 101, a measurement apparatus 102, and a display apparatus 103. The information processing apparatus 101 can perform various processing (including processing for calculating reflection characteristic measurement conditions). The measurement apparatus 102 can perform BRDF measurement processing. The display apparatus 103 can display a CG image generated by the information processing apparatus 101. The measurement apparatus 102 is not limited to a specific type in measurement method thereof. For example, a BRDF measurement device employable in the present exemplary embodiment is a gonioreflectometer. Alternatively, the line sensor discussed in Japanese Unexamined Patent Application Publication (Translation of PCT Application) No. 2002-500754 is employable for the BRDF measurement. The gonioreflectometer is a measurement apparatus that includes a light source and a light receiving sensor. The gonioreflectometer can realize two-axis alteration with respect to the angle of light that enters a sample from the light source and the angle of light traveling from the sample to the light receiving sensor. The gonioreflectometer can perform the BRDF measurement processing for various combinations of the incidence angle and the outgoing angle. Further, a display mechanism of the display apparatus 103 is not limited to a specific type. For example, a liquid crystal display device, a plasma display device, or an organic EL display device is employable as the display apparatus 103. Further, a liquid crystal projector, a digital light processing (DLP) projector, or any other screen on which a video can be projected is usable.

Figure 2:
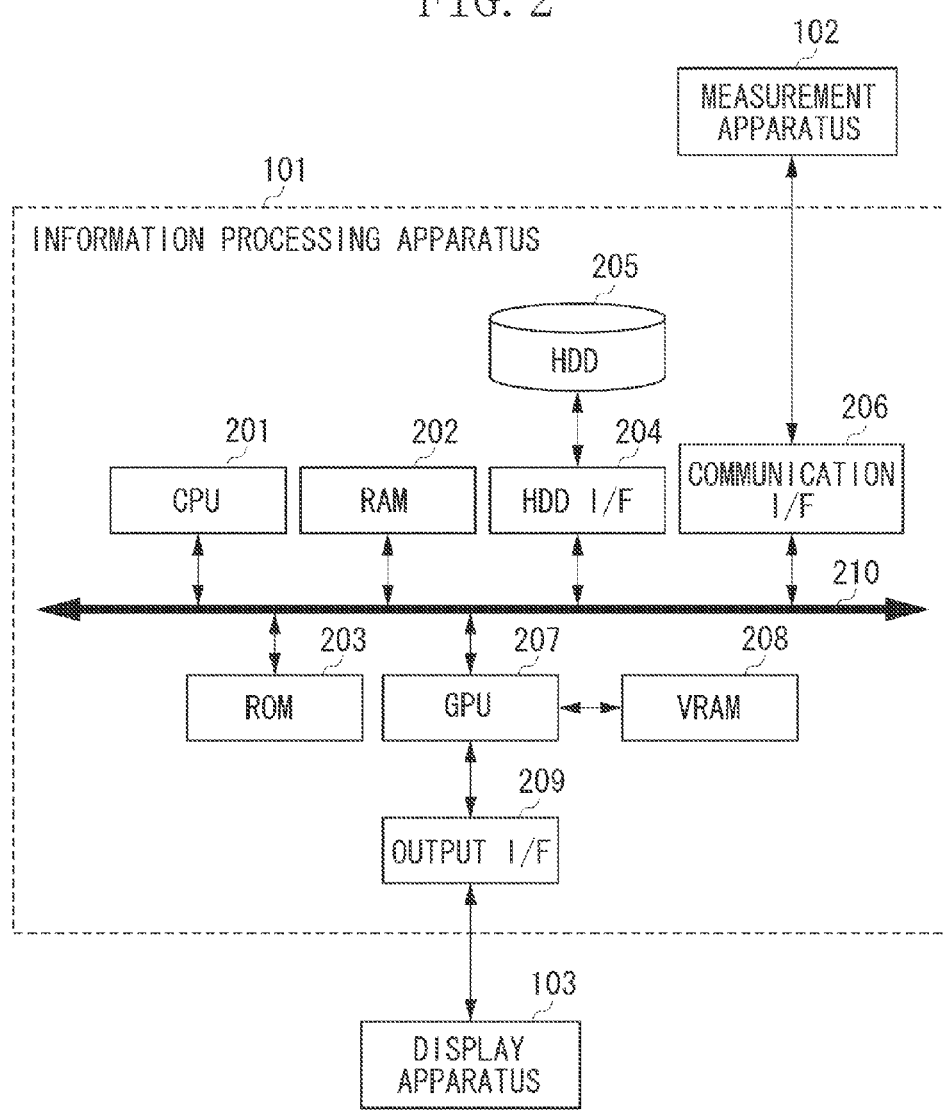
FIG. 2 is a block diagram illustrating a configuration of an information processing apparatus according to a first exemplary embodiment.

FIG. 2 illustrates a configuration of the information processing apparatus 101 (hereinafter, referred to as processing apparatus 101).

The processing apparatus 101 includes a central processing unit (CPU) 201, a random access memory (RAM) 202, a read only memory (ROM) 203, a hard disk drive (HDD) interface (I/F) 204, an HDD 205, a communication I/F 206, a graphics processing unit (GPU) 207, a video random access memory (VRAM) 208, an output I/F 209, and a system bus 210.

The CPU 201 is a control unit configured to execute each program loaded into the RAM 202 (i.e., a work memory) from the ROM 203 and the HDD 205 to control each constituent component of the processing apparatus 101 via the system bus 210. For example, the HDD I/F 204 is a serial advanced technology attachment (ATA) interface. The HDD 205, which serves as a secondary storage apparatus, is connected to the system bus 210 via the HDD I/F 204. The CPU 201 can read data from the HDD 205 via the HDD I/F 204 and can write data to the HDD 205 via the HDD I/F 204. Further, the CPU 201 can develop the stored data from the HDD 205 to the RAM 202 and can store the developed data from the RAM 202 to the HDD 205. The CPU 201 regards data developed on the RAM 202 as a program and can execute the developed data. The secondary storage apparatus is not limited to the HDD and can be another storage device (e.g., a flash memory or an optical disk drive). For example, the communication I/F 206 is a recommended standard (RS)232C interface, which connects the processing apparatus 101 to the measurement apparatus 102. The processing apparatus 101 and the measurement apparatus 102 can transmit and receive BRDF measurement conditions and measurement results via the communication I/F 206. The GPU 207 is a processor that can process an image to be output to the display apparatus 103 via the output I/F 209. The VRAM 208 is a memory that is functionally operable as a work memory for the GPU 207. The configuration of the processing apparatus 101 is not limited to the above-mentioned example and can be modified in various ways if similar effects can be obtained.

Figure 3:
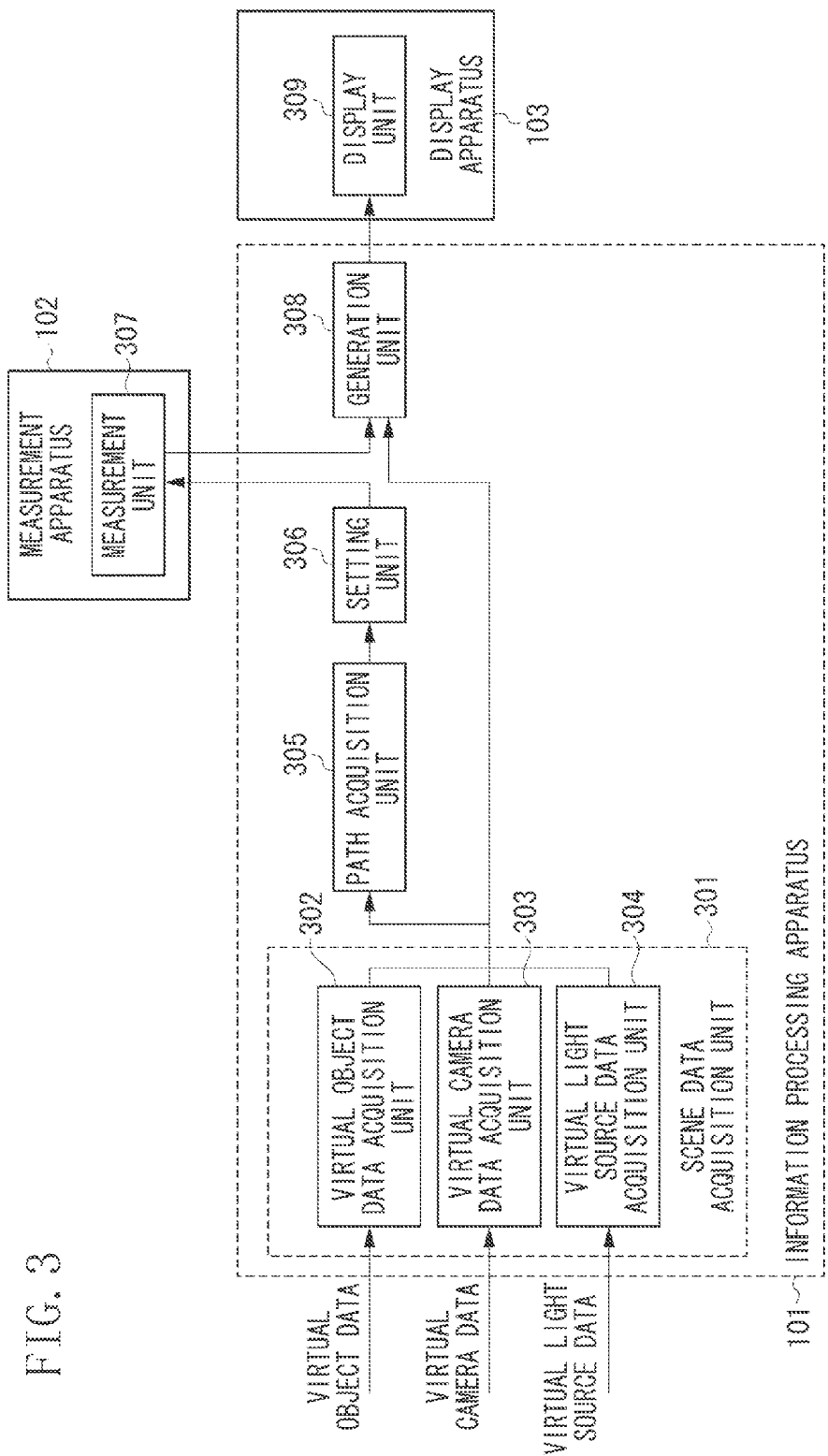
FIG. 3 is a block diagram illustrating a configuration of the reflection characteristic measurement system according to the first exemplary embodiment.

Next, processing that can be performed by the processing apparatus 101 according to the present exemplary embodiment will be described in detail below. FIG. 3 is a block diagram illustrating processing blocks of the measurement system according to the present exemplary embodiment. In the present exemplary embodiment, the processing apparatus 101 is functionally operable as each block illustrated in FIG. 3 when the CPU 201 executes a program loaded from the ROM 203 to realize processing of a flowchart illustrated in FIG. 4 in such a way as to control each constituent component of the processing apparatus 101. Processing that can be performed by the processing apparatus 101 will be described with reference to FIGS. 3 and 4.

First, in step S401, a scene data acquisition unit 301 reads scene data from the secondary storage apparatus (e.g., the HDD 205) via the HDD I/F 204. The scene data indicates information about a CG virtual space to be generated. The scene data includes at least virtual object data, virtual camera data, and virtual light source data. The virtual object data indicates information about a virtual object that is present in the virtual space. The virtual object data includes at least data representing the position and shape of the virtual object. Further, the virtual camera data indicates information about a virtual camera that can observe the virtual object in the virtual space and can capture an image of the virtual object. The virtual camera data includes at least data representing the position and orientation of the virtual camera. The virtual camera data further includes the size of a sensor (i.e., an imaging plane) provided in the virtual camera and the number of pixels that cooperatively constitute the sensor, which are information required to identify a pixel of the sensor where a light beam has reached the virtual camera. The virtual light source data indicates information about a light source that can illuminate the virtual object in the virtual space. The virtual light source data includes at least data representing the type and intensity of a light source model. In the present exemplary embodiment, the light source model is a point light source. In this case, information required to identify the point light source is the position of the light source. Therefore, the virtual light source data according to the present exemplary embodiment includes data representing the light source position.

Figure 5:
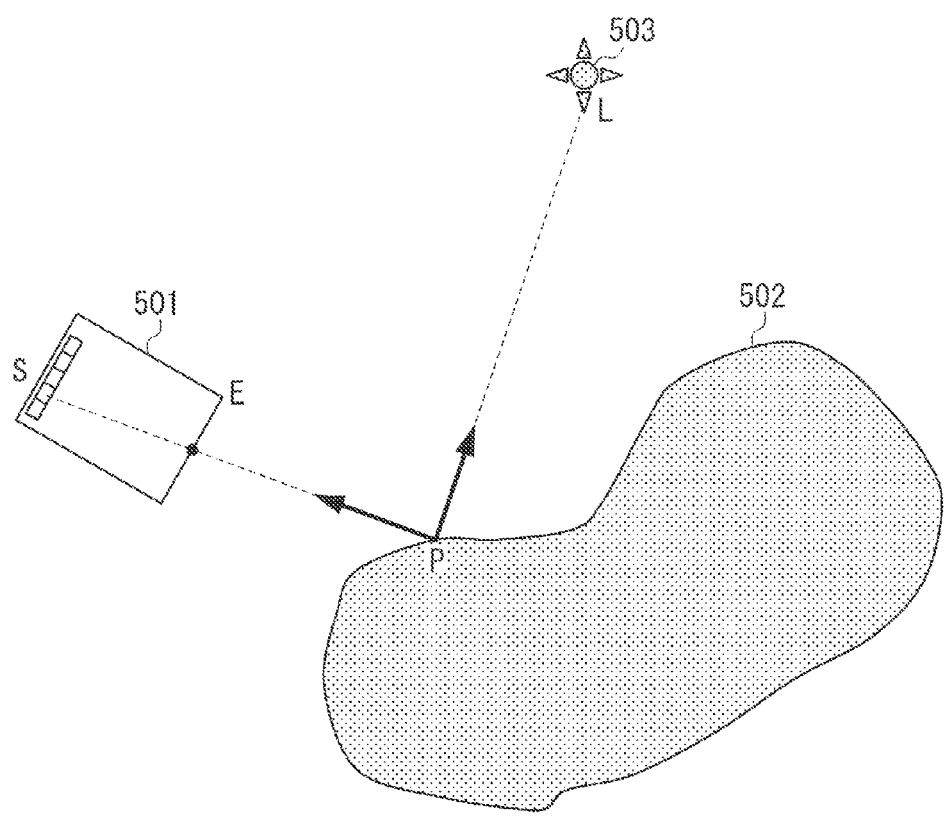
FIG. 5 illustrates a reflection of light on a virtual object.

FIG. 5 illustrates an example of the virtual space indicated by the scene data. A virtual camera 501, a virtual object 502, and a virtual light source 503 are present in the virtual space indicated by the scene data. The light beam emitted from the virtual light source 503 (i.e., the point light source) is reflected at a point P on the virtual object 502. Then, the light beam passes through a pinhole E of the virtual camera 501 and enters a pixel S. In the present exemplary embodiment, both the incidence angle and the outgoing angle of the light at the point P are used as reflection characteristic measurement conditions. The scene data acquisition unit 301 includes a virtual object data acquisition unit 302, a virtual camera data acquisition unit 303, and a virtual light source data acquisition unit 304, each of which can acquire corresponding virtual space information. The scene data acquisition unit 301 can output the acquired scene data to a path acquisition unit 305 and a generation unit 308. As a modified embodiment, the virtual object data acquisition unit 302, the virtual camera data acquisition unit 303, and the virtual light source data acquisition unit 304 can be constituted by a single acquisition unit so that the above-mentioned respective data can be collectively acquired.

In step S402, the path acquisition unit 305 acquires a light beam path along which the light beam emitted from the virtual light source travels in the virtual space until the light beam reaches each pixel of the virtual camera, based on the scene data output from the scene data acquisition unit 301. The processing to be performed in step S402 will be described in detail below. In the present exemplary embodiment, the light beam path can be expressed by using coordinate data of the light source L, coordinate data of the pinhole E or the pixel S, and coordinate data of the reflection point P on the virtual object. However, the information to be output as the light beam path is not limited to the above-mentioned example and can be any information that defines a route along which the light beam travels. The path acquisition unit 305 outputs the acquired light beam path information to the setting unit 306.

In step S403, the setting unit 306 sets measurement conditions for measuring reflection characteristics required to generate a CG image, based on the light beam path output from the path acquisition unit 305. The processing to be performed in step S403 will be described in detail below. The measurement unit 307 performs reflection characteristic measurement processing based on the measurement conditions set by the setting unit 306 in step S403 and outputs the measured reflection characteristics to the generation unit 308. In step S404, the generation unit 308 acquires the reflection characteristics received from the measurement unit 307.

In step S405, the generation unit 308 generates a CG image based on the reflection characteristics output from the measurement apparatus 102 and the reflection characteristics output from the scene data acquisition unit 301. The CG image generated in step S405 is an image of the virtual object that reflects the texture of an actual object (i.e., a real object), which is a reflection characteristic measurement target. More specifically, the virtual object included in the image generated in this case has a predetermined shape as if it is created with a material of a reflection characteristic measurement target object in a state where it is observed from a predetermined viewpoint. A pixel value of each pixel that constitutes the CG image can be determined based on radiance of light that enters each pixel of the virtual camera. The following formula expresses the radiance $L_r$ of light that enters a specific pixel from the point P on the virtual object.

[Formula 1]

$$L_r = L_i f_r(\vec{\omega}_i, \vec{\omega}_o)\max(0, \vec{n} \cdot \vec{\omega}_i) \quad (1)$$

In the formula (1), $L_i$ represents the quantity of incident light at the point P on the virtual object corresponding to the light beam that enters the pixel, n represents a normal vector at the point P, and $f_r$ represents BRDF corresponding to an incident light vector $\omega_i$ and an outgoing light vector $\omega_o$ of the incident light at the point P. The generation unit 308 generates the CG image by applying the formula (1) to all pixels that constitute the virtual camera. Further, the radiance $L_r$ calculated using the formula (1) can be directly used as a pixel value of the CG image. Alternatively, a processed value of the radiance $L_r$ having been subjected to tone mapping (e.g., gamma correction) can be usable.

Figure 4:
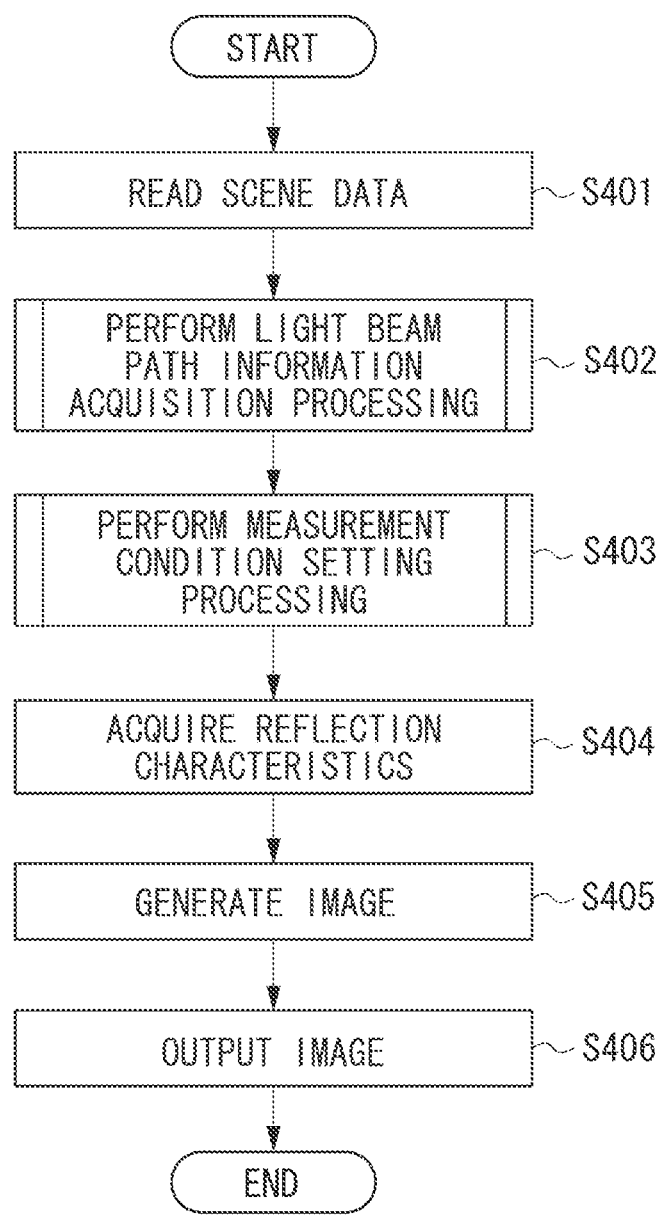
FIG. 4 is a flowchart illustrating processing that can be performed by the information processing apparatus according to the first exemplary embodiment.

Finally, in step S406, the generation unit 308 outputs the CG image generated in step S405 to the display unit 309 of the display apparatus 103 and terminates the processing of the flowchart illustrated in FIG. 4. The display unit 309 receives the CG image output from the generation unit 308 and displays the CG image. The processing apparatus 101 according to the present exemplary embodiment can perform the above-mentioned sequential processing.

Figure 6:
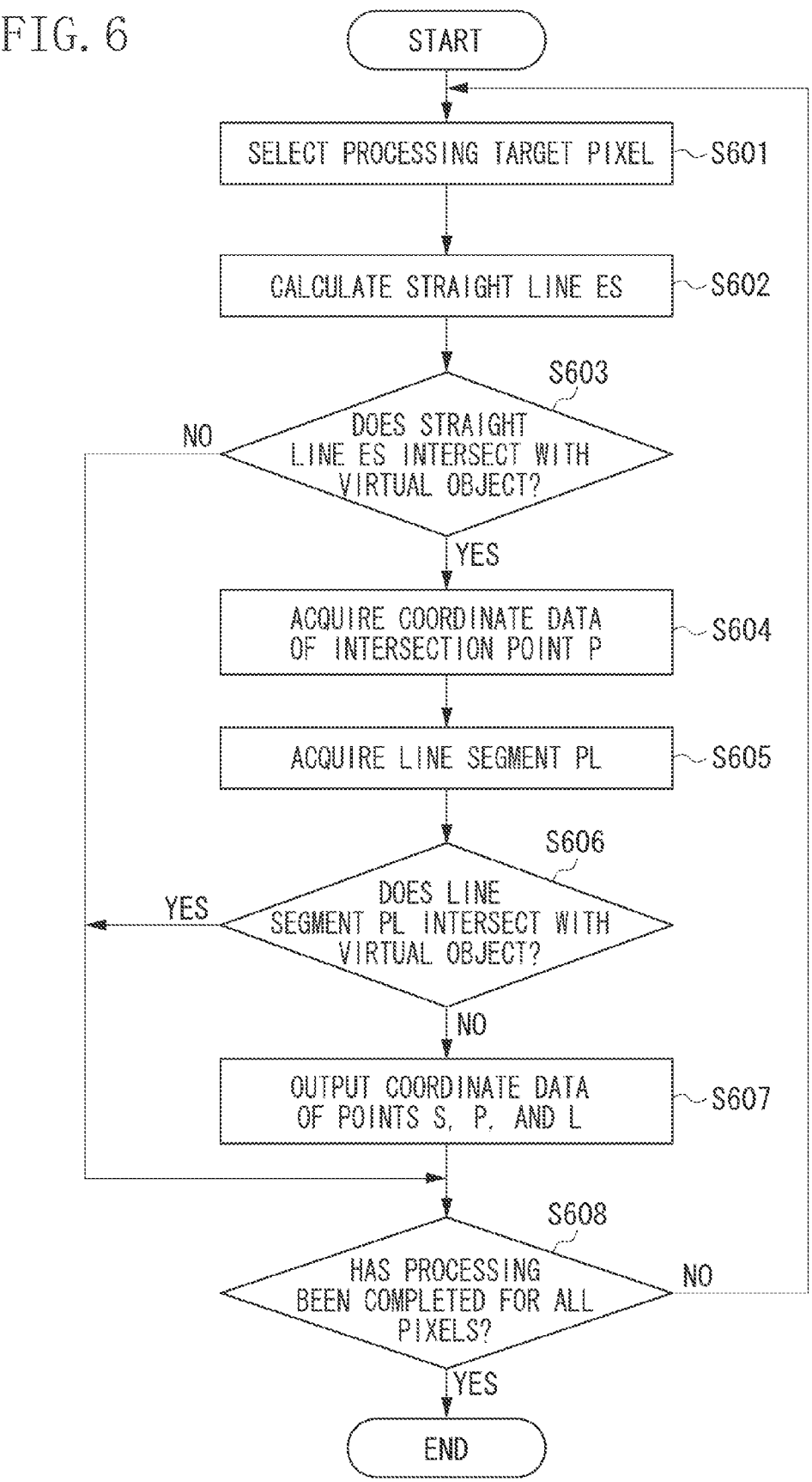
FIG. 6 is a flowchart illustrating light beam path acquisition processing according to the first exemplary embodiment.

The processing to be performed by the path acquisition unit 305 in step S402 is described in detail below with reference to a schematic view of the virtual space illustrated in FIG. 5 and a flowchart illustrated in FIG. 6. FIG. 6 is the flowchart illustrating details of the light beam path information acquisition processing to be performed in step S402. In step S601, the path acquisition unit 305 selects one of the pixels that constitute the virtual camera, indicated by the scene data, as a processing target pixel S. In step S602, the path acquisition unit 305 obtains a straight line ES passing through the pixel S and the pinhole E as a straight line representing the light beam that enters the pixel S. Since the virtual camera 501 is a pinhole camera, the light beam that enters the pixel S can be uniquely determined as the straight line ES. When the positional relationship between the pinhole E and the pixel S of the virtual camera 501 in the virtual space can be identified based on the scene data, the path acquisition unit 305 can determine the straight line ES with reference to the coordinate data of the pinhole E and the pixel S. In step S603, the path acquisition unit 305 determines whether the straight line ES intersects with the virtual object 502. Through the processing in step S603, the path acquisition unit 305 can determine whether the reflected light enters the pixel S. To determine whether the straight line ES intersects with the virtual object 502, the path acquisition unit 305 checks the presence of an intersection point at which a mesh developed on the virtual object 502 intersects with the straight line ES. The virtual object data includes, as information indicating the virtual object 502, coordinate data of a plurality of mesh points that constitute the virtual object 502. The path acquisition unit 305 can obtain an equation and a definition region of a plane indicating a mesh constituted by three mesh points that are present closest to the intersection point based on the coordinate data included in the virtual object data. In the present exemplary embodiment, to determine whether the straight line ES intersects with the virtual object 502, the path acquisition unit 305 determines whether the intersection point where the straight line ES intersects with the equation of the plane indicating each mesh is present in the definition region of each mesh. However, any other appropriate method is usable in the above-mentioned intersection determination. For example, it is useful to store information about the equation of each mesh beforehand in the virtual object data. Further, it is useful to store the definition region of each straight line that intersects with the virtual object 502 obtained beforehand. The path acquisition unit 305 can compare the data of intersecting straight lines with each other. If the path acquisition unit 305 determines that the straight line ES does not intersect with the virtual object 502 (No in step S603), it means that the reflected light does not enter the pixel S. Therefore, the operation proceeds to step S608. If the path acquisition unit 305 determines that the straight line ES intersects with the virtual object 502 (Yes in step S603), the operation proceeds to step S604.

In step S604, the path acquisition unit 305 acquires coordinate data of the intersection point P where the straight line ES intersects with the virtual object 502. In a case where there is a plurality of intersection points where the straight line ES intersects with the virtual object 502, the path acquisition unit 305 outputs coordinate data of an intersection point closest to the pinhole E as the coordinate data of the intersection point P. More specifically, points on the back side of the virtual object 502 are not determined as the intersection point P where the straight line ES intersects with the virtual object 502. Therefore, points on the back side of the virtual object 502 where the reflected light cannot enter the pixel S can be surely excluded. In step S605, the path acquisition unit 305 obtains a line segment PL passing through the light source L and the intersection point P. Then, in step S606, the path acquisition unit 305 determines whether the line segment PL intersects with the virtual object 502 at any point other than the point P. An intersection determination method used in this case is similar to the method used in step S603. Through the above-mentioned processing, the path acquisition unit 305 can determine whether the light reaches the intersection point P. If the path acquisition unit 305 determines that the line segment PL intersects with the virtual object at a point other than the point P (Yes in step S606), the light beam does not reach the intersection point P. Therefore, the path acquisition unit 305 determines there is not any path of light passing through the intersection point P, and the operation proceeds to step S608. If the path acquisition unit 305 determines that the line segment PL does not intersect with the virtual object 502 at any point other than the point P (No in step S606), there is a light beam that travels from the light source L to the intersection point P. Therefore, the operation proceeds to step S607. In step S607, the path acquisition unit 305 outputs coordinate data of the point S, the point P, and the point L that constitute the light beam path to the setting unit 306. Finally, in step S608, the path acquisition unit 305 determines whether the above-mentioned sequential processing in steps S601 to S607 has been completed for all pixels. If the path acquisition unit 305 determines that the above-mentioned sequential processing is not yet completed for all pixels (No in step S608), the operation returns to step S601. Then, the path acquisition unit 305 selects a new pixel as a processing target pixel. If it is determined that the above-mentioned sequential processing has been completed for all pixels (Yes in step S608), the path acquisition unit 305 terminates the processing of the flowchart illustrated in FIG. 6.

Figure 7:
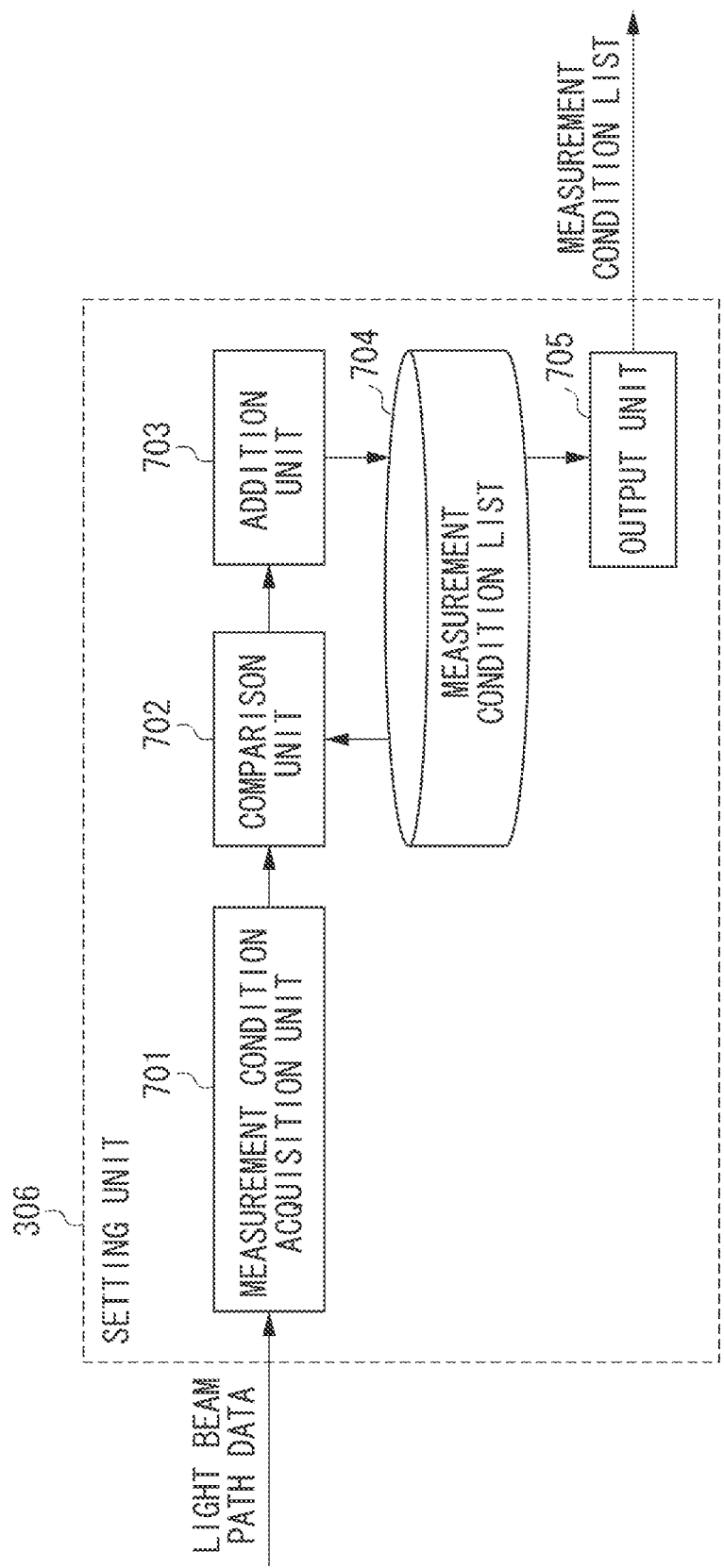
FIG. 7 is a block diagram illustrating a configuration of a setting unit according to the first exemplary embodiment.
Figure 8:
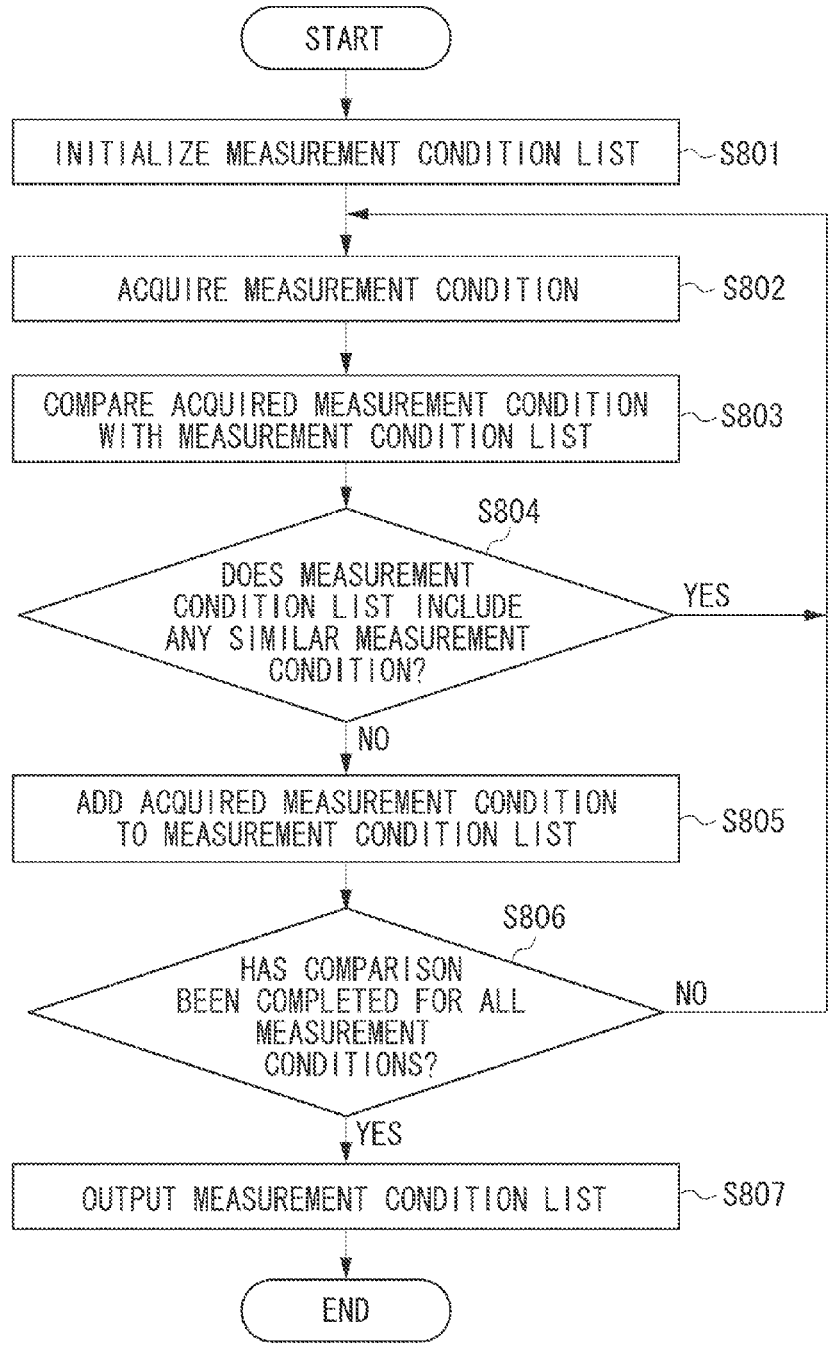
FIG. 8 is a flowchart illustrating measurement condition setting processing according to the first exemplary embodiment.

The path acquisition unit 305 can perform the above-mentioned sequential processing. Now, the processing that can be performed by the setting unit 306 in step S403 is described in detail below with reference to a block diagram illustrated in FIG. 7 and a flowchart illustrated in FIG. 8. FIG. 7 is the block diagram illustrating a configuration of the setting unit 306. FIG. 8 is the flowchart illustrating details of the processing to be performed in step S403.

In step S801, the setting unit 306 initializes a measurement condition list 704 as a null set. The measurement condition list 704 is a list of BRDF measurement conditions to be output to the measurement apparatus 102. BRDF is a variable defined by parameters of light (e.g., incidence angle and outgoing angle) at a concerned point. The BRDF measurement condition can be expressed by using a set ($\omega_i$, $\omega_o$) of an incidence direction vector $\omega_i$ and an outgoing direction vector $\omega_o$ of light at a concerned point. The measurement apparatus 102 performs a BRDF measurement operation by changing the positional relationship between the light source and the sensor based on the measurement condition. However, the above-mentioned set of two vectors can be replaced by a set of an incident light angle and an outgoing light angle. The initialization processing can be skipped if it has already been performed at the time when the processing according to the present exemplary embodiment has been completed.

In step S802, a measurement condition acquisition unit 701 (hereinafter, referred to as a condition acquisition unit 701) acquires a BRDF measurement condition that corresponds to the virtual camera light beam path output from the path acquisition unit 305. Coordinate data of the point S, the point P, and the point L can be known beforehand with reference to the output from the path acquisition unit 305. Therefore, the condition acquisition unit 701 obtains the vector set ($\omega_i$, $\omega_o$) by substituting the coordinate data of the point S, the point P, and the point L in the following formula.

[Formula 2]

$$\vec{\omega_i} = \frac{\vec{L} - \vec{P}}{|\vec{L} - \vec{P}|} \quad (2)$$

[Formula 3]

$$\vec{\omega_o} = \frac{\vec{S} - \vec{L}}{|\vec{S} - \vec{L}|} \quad (3)$$

In many cases, the incident light vector and the outgoing light vector that represent a sampling point in the BRDF measurement can be expressed in a tangent space. If "n" represents a normal vector at the intersection point P, "t"

represents a tangent vector, and "b" represents a subordinate normal vector, the following formula can be used to express a matrix T that converts a world coordinate system into a tangent space coordinate system.

[Formula 4]

$$T = (\vec{t}\ \vec{b}\ \vec{n})^t \quad (4)$$

Therefore, the measurement condition acquisition unit 701 can convert the coordinate system into the tangent space by using the matrix T. In the following description, it is presumed that the incident light vector and the outgoing light vector at a sampling point are already converted into the coordinate system of the tangent space. The condition acquisition unit 701 outputs the acquired measurement condition to a comparison unit 702. According to the above-mentioned processing, the measurement condition corresponding to a path of light that is reflected on the virtual object 502 and enters the virtual camera 501 can be determined as a candidate of the measurement condition to be used in the reflection characteristic measurement. More specifically, a measurement condition to be used in the measurement can be selected from a plurality of measurement conditions except for reflection characteristic measurement conditions not used in generation of a virtual image. Therefore, it is feasible to reduce the time required for the reflection characteristic measurement and the data amount of measurement results. However, excluding all of the reflection characteristic measurement conditions not used in the virtual image generation is not necessarily essential. For example, it is unnecessary to exclude frequently used reflection characteristics regardless of necessity in the generation of the present virtual image, so that such reflection characteristics can be referred to in generation of another virtual image.

In step S803, the comparison unit 702 compares the measurement condition acquired from the condition acquisition unit 701 with the measurement conditions already stored in the measurement condition list 704. The comparison unit 702 calculates a degree of similarity between the measurement condition acquired from the condition acquisition unit 701 and the measurement conditions stored in the measurement condition list 704. The comparison unit 702 determines that the compared measurement conditions are similar to each other based on the fact as to whether the calculated degree of similarity exceeds a predetermined threshold level. The comparison unit 702 calculates a degree of similarity "d" between two measurement conditions ($\omega_{i1}$, $\omega_{o1}$) and ($\omega_{i2}$, $\omega_{o2}$) in such a way as to reflect the moving distance of each of the light source and the light receiving unit of the measurement apparatus 102 moving on a spherical surface. More specifically, the comparison unit 702 calculates the similarity "d" by using the following formula with reference to a geodesic line distance between two unit vectors extending on a unit spherical surface.

[Formula 5]

$$d = |\arccos(\vec{\omega}_{i1} \cdot \vec{\omega}_{i2})| + |\arccos(\vec{\omega}_{o1} \cdot \vec{\omega}_{o2})| \quad (5)$$

The method for determining the degree of similarity between compared measurement conditions is not limited to the above-mentioned example. It is useful to use the Euclidean distance between two points, which are two measurement conditions that can be expressed as points in a four-dimensional space. Further, the variable can be weighted by the characteristics of the measurement apparatus 102.

In step S804, the comparison unit 702 determines whether the measurement condition list 704 includes any measurement condition similar to the measurement condition acquired from the condition acquisition unit 701. If it is determined that the measurement condition list 704 includes a similar measurement condition (Yes in step S804), the operation returns to step S802 to acquire a new measurement condition corresponding to another pixel. If it is determined that the measurement condition list 704 does not include any similar measurement condition (No in step S804), the comparison unit 702 outputs the measurement condition acquired from the condition acquisition unit 701 to an addition unit 703.

In step S805, the addition unit 703 adds the measurement condition output from the comparison unit 702 to the measurement condition list 704. In step S806, the comparison unit 702 determines whether the comparison processing has been completed for all measurement conditions. If it is determined that the comparison processing is not yet completed for all measurement conditions (No in step S806), the operation returns to step S802 to acquire a new measurement condition corresponding to another pixel. If it is determined that the comparison processing has been completed for all measurement conditions (Yes in step S806), the operation proceeds to step S807. Finally, in step S807, an output unit 705 reads the measurement condition list 704 and outputs the measurement condition list 704 to the measurement apparatus 102. The setting unit 306 terminates the processing of the flowchart illustrated in FIG. 8.

The processing apparatus 101 according to the first exemplary embodiment can perform the above-mentioned sequential processing. The above-mentioned processing is advantageous in that a great reduction can be expected in both BRDF measurement time and measurement data amount because a CG image can be generated by measuring only the BRDF data required in the generation of the CG image. For example, when an angular resolution is 1 deg, the total number of BRDF measurement angle sets is approximately 690,000,000. On the other hand, according to the present exemplary embodiment, the total number of measurement angle sets required to generate a CG image having a resolution of 1920×1080 pixels is equal to or less than 2,070,000. In other words, the rate of reduction is equal to or greater than 99%.

In the present exemplary embodiment, the scene data acquisition unit 301 is functionally operable as an information acquisition unit configured to acquire information indicating the positional relationship among a virtual light source, a virtual object, and a virtual viewpoint, as well as information indicating a surface shape of the virtual object where light emitted from the virtual light source enters. Further, the path acquisition unit 305 is functionally operable as a path acquisition unit configured to acquire a path of light along which light emitted from the virtual light source is reflected on the virtual object and reaches the virtual viewpoint with reference to the information indicating the positional relationship and the information indicating the shape. The setting unit 306 is functionally operable as a determination unit configured to determine a part of measurement conditions that can be used for the reflection characteristic measurement, as a measurement condition to be used in the reflection characteristic measurement, based on the information indicating the positional relationship and the information indicating the shape. The generation unit 308 is functionally operable as a generation unit configured to acquire reflection characteristics of a real object measured based on the measurement condition determined by the determination unit and to generate the virtual image with reference to the acquired reflection characteristics. The output unit 705 is functionally operable as an output unit configured to output the measurement condition determined by the determination unit to a measurement unit configured to measure reflection characteristics of the real object. The measurement unit 307 is functionally operable as a measurement unit configured to measure reflection characteristics of the real object.

Figure 9:
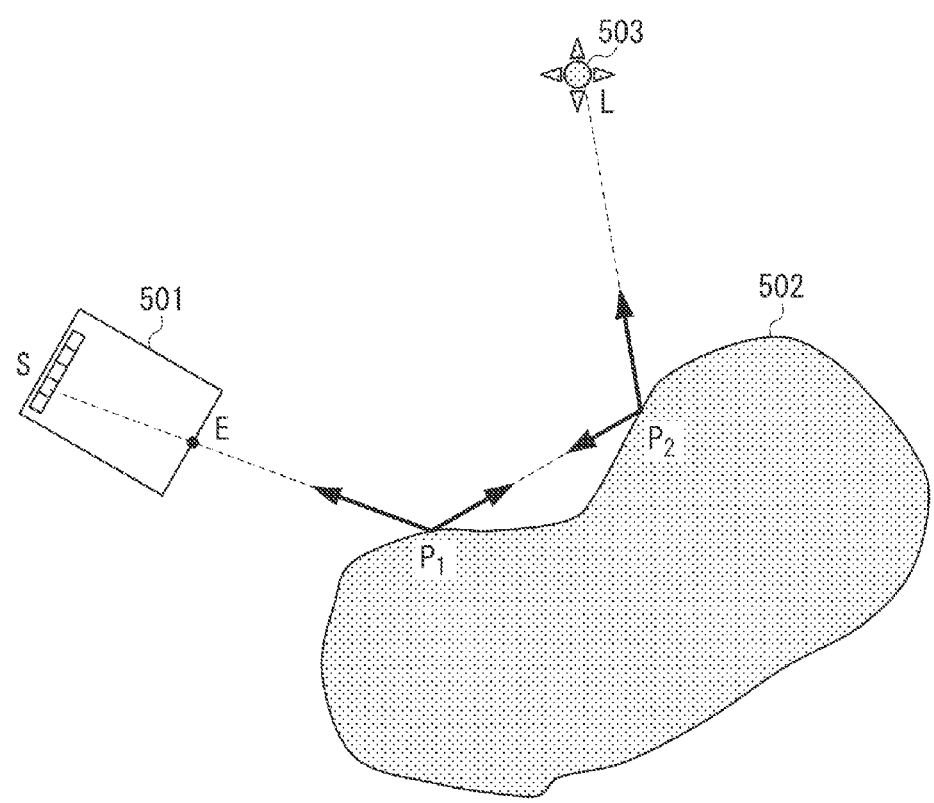
FIG. 9 illustrates a secondary reflection of light on a virtual object.

As described above, in the first exemplary embodiment, only a direct light is taken into consideration when a CG image is generated. More specifically, the direct light is a light beam that is emitted from the virtual light source and reaches the virtual camera after being once reflected on the virtual object. Measurement condition setting according to a second exemplary embodiment is characterized in that an indirect light is taken into consideration. The indirect light is a light beam that causes a secondary reflection on a surface of the virtual object to irradiate the virtual camera. FIG. 9 is a schematic diagram illustrating an example of the secondary reflection occurring in the virtual space. A light beam emitted from the light source 503 reaches a point $P_2$ on the virtual object 502. Then, the light beam reflected at the point $P_2$ reaches a point $P_1$. The light beam reflected at the point $P_1$ enters the pixel S. When the indirect light is taken into consideration in generating a CG image, it becomes necessary to measure reflection characteristics along a light beam path L-$P_2$-$P_1$ and reflection characteristics along a light beam path $P_2$-$P_1$-S.

Figure 10B:
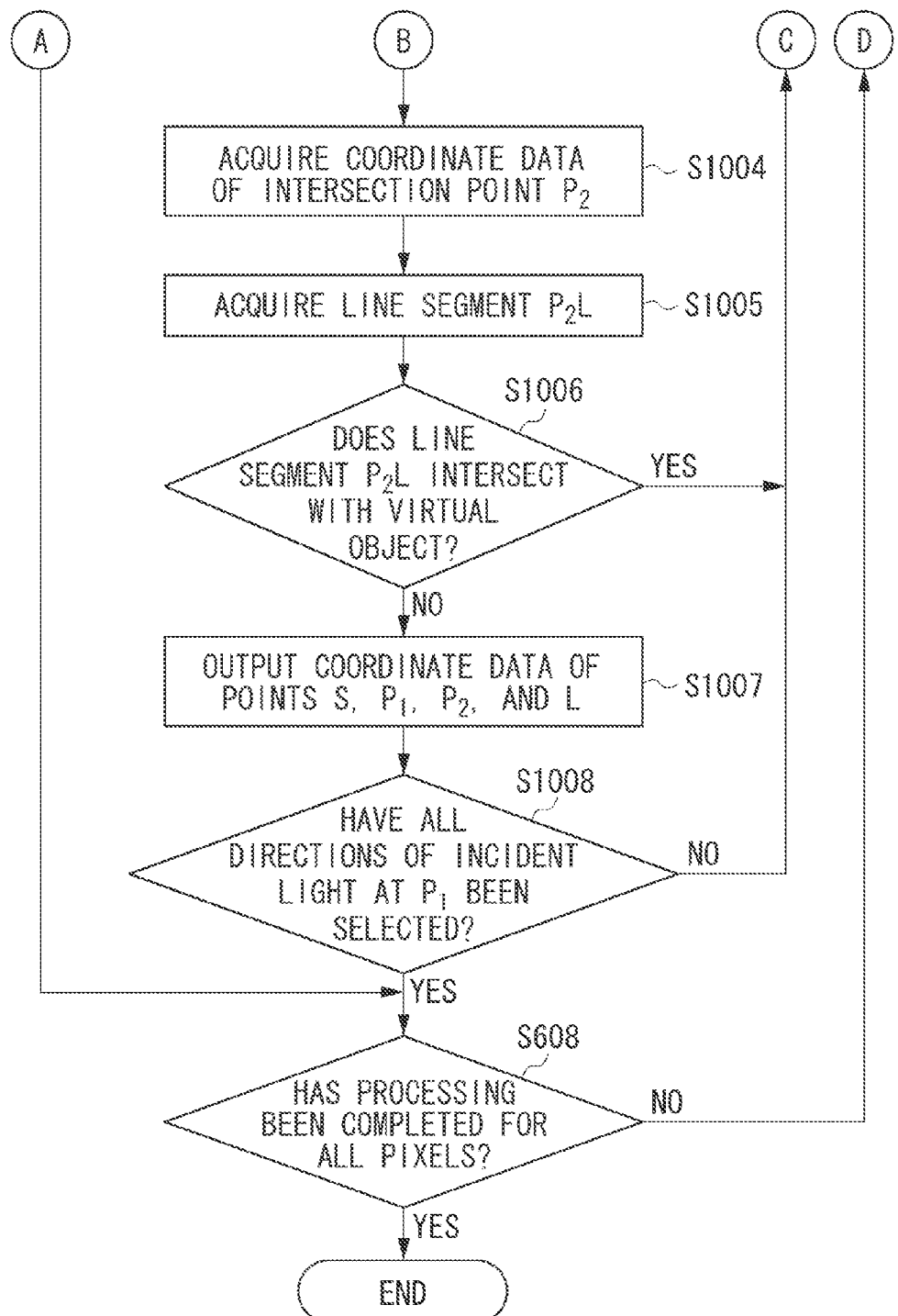
FIG. 10, composed of FIGS. 10A and 10B, is a flowchart illustrating light beam path acquisition processing according to a second exemplary embodiment.

The present exemplary embodiment is different from the first exemplary embodiment in the contents of light beam path acquisition processing to be performed in step S402 and measurement condition acquisition processing to be performed in step S802. Hereinafter, the light beam path acquisition processing that can be performed by the processing apparatus 101 according to the present exemplary embodiment will be described in detail below with reference to the schematic diagram illustrated in FIG. 9 and a flowchart illustrated in FIG. 10. In FIGS. 6 and 10, if the processing contents are similar, the same reference numbers are allocated to corresponding steps. Redundant description thereof will be avoided.

In step S1001, the path acquisition unit 305 acquires coordinate data of an intersection point where the straight line ES intersects with the virtual object 502, as coordinate data of the point $P_1$ where the reflected light enters. In a case where there is a plurality of intersection points, the path acquisition unit 305 acquires coordinate data of an intersection point closest to the pinhole E, as coordinate data of the point $P_1$. Next, in step S1002, the path acquisition unit 305 selects the direction of the incident light beam at the point $P_1$ and acquires the straight line corresponding to the selected light beam direction. Every direction around the point $P_1$ is set beforehand as a candidate of the direction of the incident light beam at the point $P_1$. In the present exemplary embodiment, the path acquisition unit 305 randomly selects one of the setting directions. Any other appropriate rule is employable to realize the above-mentioned selection of the incidence direction. In step S1003, the path acquisition unit 305 determines whether the selected incident light intersects with the virtual object 502. Through the above-mentioned processing, the path acquisition unit 305 can determine whether the selected incident light is the reflected light from the virtual object 502. If the path acquisition unit 305 determines that the selected incident light does not intersect with the virtual object 502 (No in step S1003), there is not any reflected light that enters the point $P_1$ along the selected direction. Therefore, the operation returns to step S1002 to select a new direction. If the path acquisition unit 305 determines that the selected incident light intersects with the virtual object 502 (Yes in step S1003), the operation proceeds to step S1004.

In step S1004, the path acquisition unit 305 acquires coordinate data of the intersection point $P_2$ where the incident light reflected at the point $P_1$ intersects with the virtual object 502. If there is a plurality of intersection points, the path acquisition unit 305 acquires an intersection point closest to the point $P_1$ as the coordinate data of the point $P_2$. In step S1005, the path acquisition unit 305 acquires a line segment $P_2$L passing through the point L and the point $P_2$. Then, in step S1006, the path acquisition unit 305 determines whether the line segment $P_2$L intersects with the virtual object 502 at any point other than the point $P_2$. Through the above-mentioned processing, the path acquisition unit 305 can determine whether light that travels from the light source L to the point $P_2$ is present. If the path acquisition unit 305 determines that the line segment $P_2$L intersects with the virtual object 502 at a point other than the point $P_2$ (Yes in step S1006), the light emitted from the light source L does not reach the point $P_2$ because the light is shielded by the virtual object 502. The path acquisition unit 305 determines that there is not any secondary indirect light passing through the points $P_1$ and $P_2$. Thus, the operation returns to step S1002. If the path acquisition unit 305 determines that the line segment $P_2$L does not intersect with the virtual object 502 at any point other than the point $P_2$ (No in step S1006), the operation proceeds to step S1007. In step S1007, the path acquisition unit 305 outputs coordinate data of the point S, the point $P_1$, the point $P_2$, and the point L, which cooperatively define a light beam path of the indirect light, to the setting unit 306. Then, the operation proceeds to step S1008. In step S1008, the path acquisition unit 305 determines whether all directions of the incident light at the point $P_1$ have been thoroughly selected. If the path acquisition unit 305 determines that all directions of the incident light have not yet been selected (No in step S1008), the operation returns to step S1002 to select a new direction. If the path acquisition unit 305 determines that all directions of the incident light have already been selected (Yes in step S1008), the operation proceeds to step S608. In step S608, the path acquisition unit 305 determines whether the above-mentioned sequential processing has been completed for all pixels, as mentioned above in the first exemplary embodiment. Then, the path acquisition unit 305 terminates the processing of the flowchart illustrated in FIG. 10.

The path acquisition unit 305 according to the present exemplary embodiment can perform the above-mentioned sequential processing. The path acquisition unit according to the present exemplary embodiment outputs the coordinate data of four points S, $P_1$, $P_2$, and L that cooperative define the light beam path. Therefore, the present exemplary embodiment is different from the first exemplary embodiment in the processing to be performed by the condition acquisition unit 701. The condition acquisition unit 701 according to the present exemplary embodiment acquires a first measurement condition derived from the reflection direction at the point $P_1$ and a second measurement condition derived from the reflection direction at the point $P_2$. If a vector set ($\omega_{i1}$, $\omega_{o1}$) represents the first measurement condition and a vector set ($\omega_{i2}$, $\omega_{o2}$) represents the second measurement condition, the following formulae can be used to express respective measurement conditions.

[Formula 6]

$$\vec{\omega}_{i,P_1} = \frac{\vec{P_2} - \vec{P_1}}{|\vec{P_2} - \vec{P_1}|} \qquad (6)$$

$$\vec{\omega}_{o,P_1} = \frac{\vec{S} - \vec{P_1}}{|\vec{S} - \vec{P_1}|}$$

-continued

[Formula 7]

$$\vec{\omega_{i,P_2}} = \frac{\vec{L} - \vec{P_2}}{|\vec{L} - \vec{P_2}|} \qquad (7)$$

$$\vec{\omega_{o,P_2}} = \frac{\vec{P_1} - \vec{P_2}}{|\vec{P_1} - \vec{P_2}|}$$

The condition acquisition unit 701 substitutes the position vectors represented by the coordinate data of four points output from the path acquisition unit 305 in the above-mentioned formulae 6 and 7 to acquire the first and second measurement conditions. Then, the condition acquisition unit 701 outputs the first and second measurement conditions to the comparison unit 702. The setting unit 306 performs the remaining processing as described in the first exemplary embodiment.

The processing apparatus 101 according to the present exemplary embodiment performs the above-mentioned processing. Through the above-mentioned processing, it is feasible to generate a highly accurate CG image because the measurement condition setting can be accurately performed by taking both the direct light and the indirect light into consideration. The above-mentioned light beam path acquisition method is generally referred to as a path tracing method. However, the light beam path acquisition method is not limited to the above-mentioned example. For example, other methods applicable to the above-mentioned light beam path acquisition are a photon mapping method and a bidirectional path tracing method. Further, the processing according to the present exemplary embodiment is characterized by indirect light beam path search to be performed while taking secondary reflections into consideration. However, it is useful to take higher-order reflections into consideration in the light beam path search.

Figure 11:
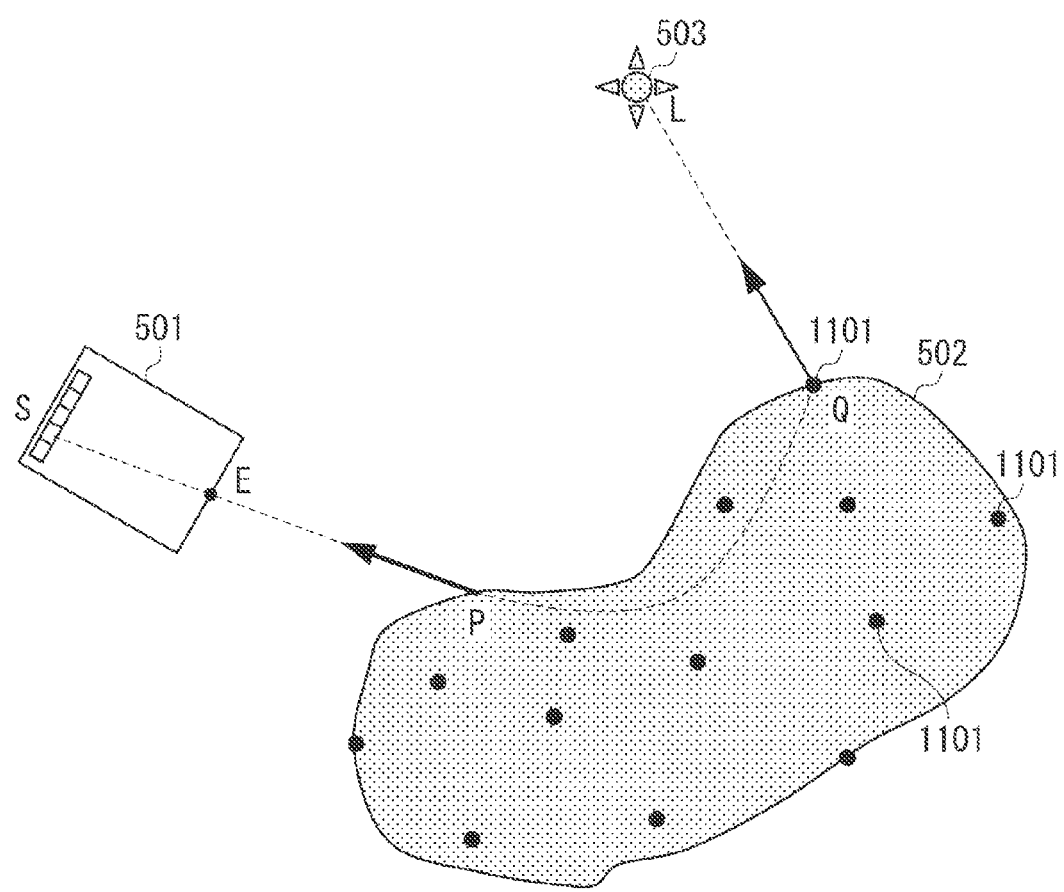
FIG. 11 illustrates a light beam path in a semitransparent object.

In the first and second exemplary embodiments, a BRDF based model has been used to describe reflection characteristics. In a third exemplary embodiment, light having entered a virtual object via its surface causes scattering in the virtual object (e.g., a semitransparent object), as described in detail below. Bidirectional scattering surface reflectance distribution function (BSSRDF) is generally usable to express reflection characteristics of such a semitransparent object. A light source used in the present inventions is only one point light source that is similar to that described in the first and second exemplary embodiments. FIG. 11 illustrates a path of light beam reflected in a semitransparent object. A light beam emitted from the light source 503 enters the virtual object 502 at the point Q. In the virtual object 502 (i.e., the semitransparent object), the light travels from the point Q to the point P while causing scattering in the virtual object 502. Then, the light goes out from the point P and enters the pixel S. BSSRDF (defining reflection characteristics of such an object) is a variable including parameters that are different from those of BRDF. The parameters of BSSRDF includes not only incident light and outgoing light directions but also coordinate data of an incident point where the light enters the object and an outgoing point where the light goes out from the object. When $\omega_i$ is an incident light vector representing the direction of the incident light, $\omega_o$ is an outgoing light vector representing the direction of the outgoing light, $x_i$ represents coordinate data of the incident point, and $x_o$ represents coordinate data of the outgoing point, the expression ($\omega_i$, $x_i$, $\omega_o$, $x_o$) indicates one set of BSSRDF measurement condition. According to the BSSRDF measurement, all points on the virtual object 502 where light enters from the light source L are candidates for the incident point, and all points on the virtual object 502 where the light goes out and travels toward the pixel S are candidates for the outgoing point. Therefore, the light beam path acquisition processing according to the present exemplary embodiment includes generating a candidate list of incident points and a candidate list of outgoing points beforehand, selecting an arbitrary combination of the incident point and the outgoing point with reference to these candidate lists, and outputting a light beam path.

Figure 12B:
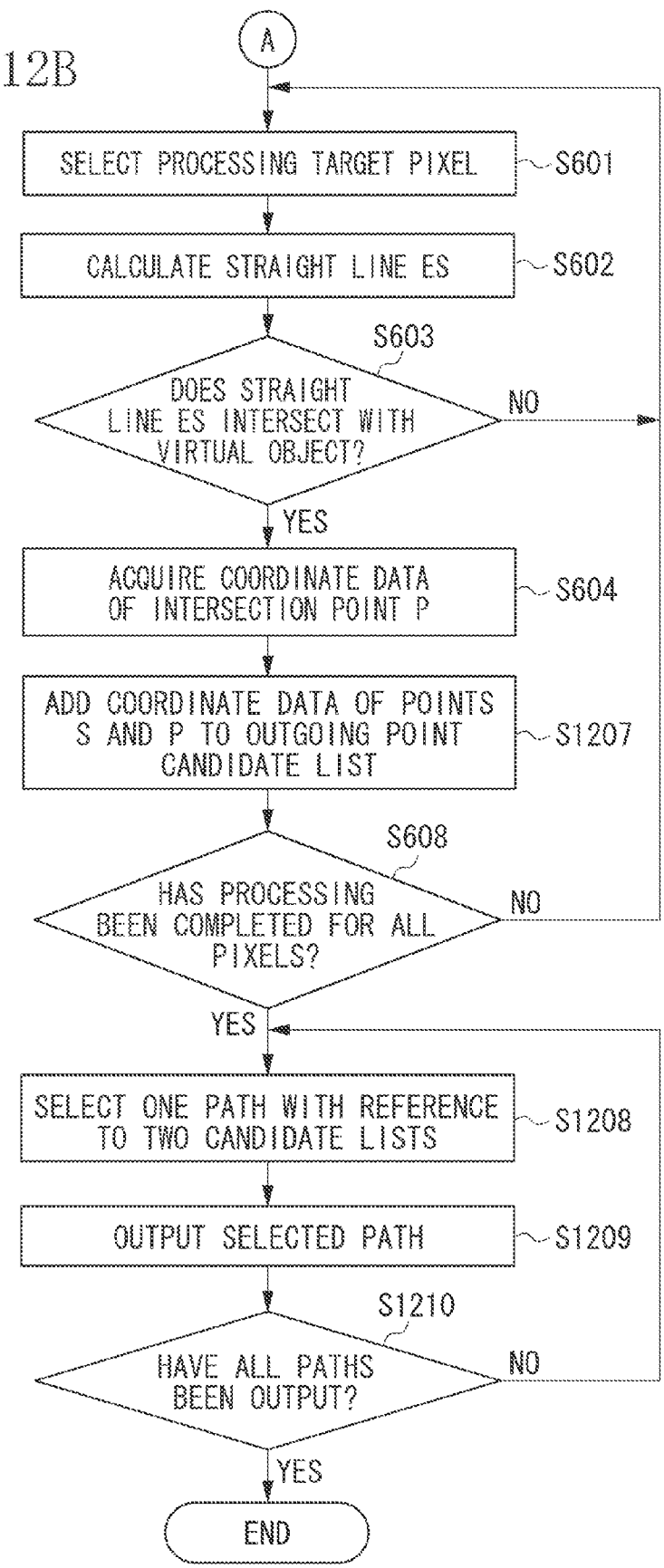
FIG. 12, composed of FIGS. 12A and 12B, is a flowchart illustrating light beam path acquisition processing according to a third exemplary embodiment.

Hereinafter, the light beam path acquisition processing according to the present exemplary embodiment will be described in detail below with reference to the schematic diagram illustrated in FIG. 11 and a flowchart illustrated in FIG. 12. In step S1201, the path acquisition unit 305 generates a point group (irradiance cache point group) to store the irradiance (irradiance cache) on a surface of the virtual object 502. In FIG. 11, each of a plurality of points 1101 is an irradiance cache point. In this case, it is desired that irradiance cache points are disposed at equi-intervals on the surface of the virtual object. For example, it is useful to locate an initial point according to the Poisson Disc Sampling method and then dispose remaining irradiance cache points 1101 at equi-intervals according to the Reaction Diffusion method. The method for generating the irradiance cache point group is not limited a specific method. For example, random numbers are usable to determine the arrangement of respective irradiance cache points, although using the random numbers is not advantageous in calculation accuracy and calculation efficiency. The path acquisition unit 305 stores coordinate data of each irradiance cache point generated in the above-mentioned step in the RAM 202. Next, in step S1202, the path acquisition unit 305 selects a cache point Q, as a candidate incident point where the light beam from the light source L enters, from the irradiance cache point group generated in step S1201.

In step S1203, the path acquisition unit 305 acquires a line segment QL passing through the point Q selected in step S1202 and the light source L. Then, in step S1204, the path acquisition unit 305 determines whether the line segment QL intersects with the virtual object 502 at a point other than the point Q. When the line segment QL intersects with the virtual object 502 at a point other than the point Q (Yes in step S1204), light emitted from the light source L does not directly enter the point Q. Therefore, the operation returns to step S1202 to select a new cache point. If the path acquisition unit 305 determines that the line segment QL does not intersect with the virtual object 502 at any point other than the point Q (No in step S1204), the operation proceeds to step S1205.

In step S1205, the path acquisition unit 305 adds the coordinate data of the point Q to an incident point candidate list stored in the RAM 202, as a candidate of the incident point where light beam emitted from the light source L enters. In step S1206, the path acquisition unit 305 determines whether selection of all cache points Q has been completed. If it is determined that the selection of all cache points Q is already completed (Yes in step S1206), the operation proceeds to step S601. If it is determined that the selection of all cache points Q is not yet completed (No in step S1206), the operation returns to step S1202 to select a new cache point Q.

In steps S601 to S604, the path acquisition unit 305 performs processing similar to that described in the first exemplary embodiment to calculate coordinate data of the point P on the virtual object 502 that corresponds to the pixel S on the virtual camera 501. Then, in step S1207, the path acquisition unit 305 adds the coordinate data of the point P calculated in step S604 to an outgoing point candidate list stored in the RAM 202. Then, in step S608, similar to the first exemplary embodiment, the path acquisition unit 305 determines whether all pixels have been processed. If it is determined that all pixels have been processed (Yes in step S608), the operation proceeds to step S1208. In step S1208, the path acquisition unit 305 selects an arbitrary combination of the incident point and the outgoing point with reference to the incident point candidate list and the outgoing point candidate list stored in the RAM 202. In the present exemplary embodiment, the combination of the incident point and the outgoing point is regarded as a light beam path. In step S1209, the path acquisition unit 305 outputs the light beam path selected in step S1208 to the setting unit 306. Then, in step S1210, the path acquisition unit 305 determines whether all selectable light beam paths have been output. If the path acquisition unit 305 determines that output of all light beam paths has not yet been completed (No in step S1210), the operation returns to step S1208 to select a new light beam path. When all light beam paths have been output (Yes in step S1210), the path acquisition unit 305 terminates the processing of the flowchart illustrated in FIG. 12.

The path acquisition unit 305 according to the present exemplary embodiment performs the above-mentioned sequential processing. Processing to be performed by the condition acquisition unit 701 is basically similar to that described in the first exemplary embodiment. However, the data acquired in the present exemplary embodiment is BSSRDF (not BRDF). Therefore, the present exemplary embodiment is differentiated in the formula to be used in the acquisition of measurement condition. The measurement condition acquired by the condition acquisition unit 701 is the data represented by the expression $(\omega_i, x_i, \omega_o, x_o)$. In this case, each parameter of the measurement condition can be calculated by using the following formula with reference to the coordinate data of the point P and the point Q output from the path acquisition unit 305 and the coordinate data of the light source L and the viewpoint E stored in the RAM 202.

[Formula 8]

$$(x_i, \vec{\omega_i}, x_o, \vec{\omega_o}) = \left( Q, \frac{\vec{L} - \vec{Q}}{|\vec{L} - \vec{Q}|}, P, \frac{\vec{P} - \vec{E}}{|\vec{P} - \vec{E}|} \right) \quad (8)$$

Further, the CG generation according to the present exemplary embodiment is performed based on BSSRDF (not BRDF) data. Therefore, the present exemplary embodiment is differentiated in the formula to be used by the generation unit 308 in the generation of an image. The radiance Lr of light that enters a specific pixel of the virtual camera can be represented by the following formula, using the coordinate data $x_o$ of the light outgoing point P and the outgoing light vector $\omega_o$.

[Formula 9]

$$L_r(x_o, \vec{\omega_o}) = \Sigma_k^{n_p} A_k L_i(x_{i,k}, \vec{\omega_{i,k}}) S(x_{i,k}, \vec{\omega_{i,k}}, x_o, \vec{\omega_o}) \max(0, \overrightarrow{n(x_{i,k})} \cdot \vec{\omega_i}) \quad (9)$$

In the formula (9), $n_p$ represents the total number of irradiance cache points, $A_k$ represents a weighting factor of the k-th irradiance cache point, $x_{ik}$ represents the position of the k-th irradiance cache point, and $\omega_{ik}$ represents a direction vector of the light beam that enters the k-th irradiance cache point. Further, $L_i(x_{ik}, \omega_{ik})$ represents the intensity of the incident light at the position $x_{ik}$ and the direction $\omega_{ik}$, S represents BSSRDF, and $n(x_{ik})$ represents a vector of the normal direction at the position $x_{ik}$.

Through the above-mentioned processing, even in a case where a CG image of a semitransparent object is to be generated, reflection characteristic measurement conditions required in the generation of the CG image can be efficiently obtained.

<Parallel Processing>

In the above-mentioned exemplary embodiments, the information processing apparatus 101 performs reflection characteristic measurement and image generation processing after completing the processing in step S403 in which all measurement conditions according to which reflection characteristics should be measured are set. However, the processing to be performed by the information processing apparatus 101 is not limited to the above-mentioned example. For example, it is useful to immediately output each measurement condition to the measurement apparatus at the time when the measurement condition is newly added to the measurement condition list, so that the measurement condition setting processing and the reflection characteristic measurement processing can be performed in parallel with each other. The method described above is advantageous in that the time required for the reflection characteristic measurement can be reduced significantly in a case where a longer time is required to derive a measurement condition. Further, if the time required for the derivation of the measurement condition is relatively short, it is advantageous to perform the reflection characteristic measurement after completing the setting of all measurement conditions, because it is feasible to determine the measurement order while taking an efficient driving path of the measurement apparatus into consideration. The time required for the reflection characteristic measurement can be reduced. Furthermore, similarly, in the processing for outputting pixel values of a CG image, it is useful to generate a pixel value of each pixel corresponding to measured reflection characteristics in parallel with the reflection characteristic measurement.

<Processing Not Relying on Similarity>

In the above-mentioned exemplary embodiments, the information processing apparatus 101 determines where there is any similar measurement condition in the measurement condition list (see step S804), and does not add any new measurement condition to the measurement condition list if a similar measurement condition is present. Alternatively, the information processing apparatus 101 can skip the above-mentioned processing. More specifically, instead of calculating the degree of similarity in step S803, the information processing apparatus 101 can add all measurement conditions corresponding to the CG image to be generated to the measurement condition list, and perform measurement based on all measurement conditions. In this case, the total number of actually measured measurement conditions increases and the measurement time increases. However, a highly accurate CG image generation can be realized.

<Comparison in the List>

The processing according to the above-mentioned exemplary embodiments includes comparing a newly acquired measurement condition with the measurement conditions included in the measurement condition list and adding no new measurement condition to the measurement condition list if the newly acquired measurement condition is similar to any one of the measurement conditions already included in the measurement condition list. However, the present inventions are not limited to the above-mentioned exemplary embodiments. For example, processing according to another exemplary embodiment includes adding all of acquired measurement conditions to the measurement condition list, comparing measurement conditions with each other in the list, and deleting duplicate measurement conditions from the list.

<Rearrangement of Measurement Condition List>

In a case where a plurality of measurement conditions is used in the measurement, it may be feasible to reduce the measurement time by appropriately rearranging the order of measuring reflection characteristics although it depends on characteristics of the measurement apparatus 102. Therefore, it is useful that the information processing apparatus 101 rearranges the measurement conditions included in the measurement condition list, and optimizes the measurement order in such a way as to be appropriate for the measurement apparatus, after generating the measurement condition list in step S403. For example, the distance between two measurement conditions ($\omega_{i1}$, $\omega_{o1}$) and ($\omega_{i2}$, $\omega_{o2}$) can be calculated by using a formula that is similar to formula (5) applied to the degree of similarity. Using the above, it is feasible to constitute a graph structure for the measurement conditions included in the measurement condition list. Further, using a dynamic planning method or any other path problem solving method makes it feasible to obtain a shortest path that passes all measurement conditions.

<Reflection Characteristic Measurement+Measurement Condition Display>

Figure 13:
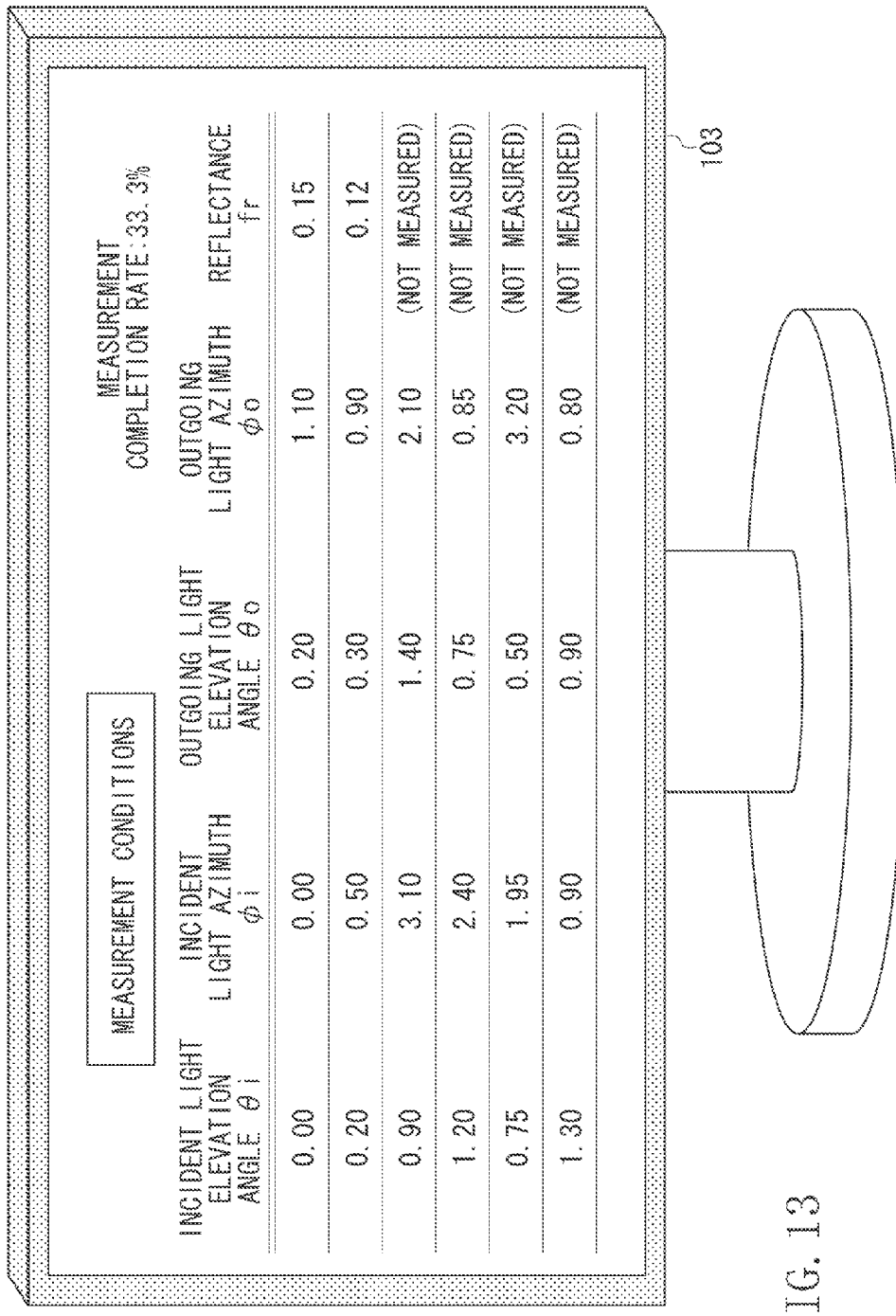
FIG. 13 illustrates a display example of measurement conditions.

It is useful to display information about the measurement condition list together with measured values on the display apparatus 103 as illustrated in FIG. 13, before or during the measurement of reflection characteristics in step S403. The display enables a user to intuitively understand the information about the measurement condition list to be used in the measurement of reflection characteristics and to check the state of progress in the measurement.

<Case where Measurement is Partly Completed>

In the above-mentioned exemplary embodiments, reflection characteristic measurement for a real object is not yet performed at the processing start timing. However, the processing can start in a state where the reflection characteristic measurement is partly completed. In this case, in step S801, the setting unit 306 stores measurement-completed measurement conditions in the measurement condition list and deletes any measurement condition other than the measurement-completed measurement conditions from measurement condition list. Then, in step S807, the output unit 705 outputs only the measurement conditions newly added to the measurement condition list in step S805 to the measurement unit 307. Through the above-mentioned processing, it becomes feasible to perform the measurement with only the newly added measurement conditions while excluding the measurement conditions that are similar to the measurement conditions already used in the reflection characteristic measurement.

<Two or More Objects>

In the above-mentioned exemplary embodiments, only one virtual object is disposed in the virtual space. However, the number of virtual objects is not limited to the illustrated example. It is feasible to generate a CG image that corresponds to a virtual space in which two or more virtual objects are disposed. In a case where each of the plurality of virtual objects disposed in the virtual space has similar texture, all virtual objects can be collectively regarded as a single virtual object in performing the measurement condition setting. On the contrary, in a case where virtual objects disposed in the virtual space are mutually different in texture, it is useful to generate a measurement condition list dedicated to a group of objects corresponding to the same texture.

<Two or More Light Sources>

In the above-mentioned exemplary embodiments, the light source disposed in the virtual space is a single point light source. However, the number of light sources is not limited to the illustrated example. Two or more light sources can be disposed in the virtual space. In this case, it is useful to perform the measurement condition setting independently for each of respective light sources. Further, it is useful to obtain a pixel value by integrating radiances deriving from each light source when a CG image is generated.

<Surface Light Source and Horizontal Light Source>

The method described in the above-mentioned exemplary embodiments is characterized by the usage of a point light source as the type of the light source model. However, the light source is not limited to a specific type. For example, the light source model type can be a surface light source or a horizontal light source. When the light source model type is the surface light source, it is useful to approximate the surface light source as numerous point light sources located on a surface of the surface light source, so that the processing can be performed in the same manner as in the case where a plurality of point light sources is used. When the light source model type is the horizontal light source, respective light sources are aligned in the same direction in the virtual space. Therefore, when ld represents the direction of each horizontal light source, the incident light vector $\omega_i$ to be acquired in step S802 can be represented by the following formula that is not dependent on the position of the point P.

[Formula 10]

$$\vec{\omega_i} = -\vec{l_d} \qquad (10)$$

Except that the value obtained by the above-mentioned formula 10 restricts the incident light vector processing to be performed in the case of using horizontal light sources is similar to the processing performed in the case of using point light sources.

<Camera Model>

The method for modeling the virtual camera described in the above-mentioned exemplary embodiments is the pinhole camera model. However, the camera model employable in the present exemplary embodiments is not limited to the above-mentioned example. More specifically, it is useful to use a camera model including a more complicated optical system in which both of aperture angle and lens aberration are taken into consideration. For example, it is useful to perform a required reflection characteristic measurement by using a camera model in which characteristics of human eyes are taken into consideration, so that an image that is similar to the scene observed from human eyes can be obtained.

<In Case of BTF Measurement>

The method described in the above-mentioned exemplary embodiments is characterized by measuring BRDF or BSSRDF as reflection characteristics. However, the type of reflection characteristics is not limited to a specific type. For example, bidirectional texture function (BTF) can be a measurement target. The bidirectional texture function is a value indicating reflection characteristics of an opaque object whose reflectance is variable depending on the position on a surface. The bidirectional texture function can be represented by $(x_o, \omega_o)$, in which $x_o$ represents texture coordinate (two-dimensional) data of the point P on the surface of a virtual object. It is useful to set a texture coordinate beforehand on each of the virtual object and a real object to acquire the texture coordinate data $x_o$. A well-known UV-Unwrap technique is usable although setting of the texture coordinate data is generally performed by a manual work.

<In Case of Diffuse Texture>

Reflection characteristics of a material similar to a diffusible and reflecting surface (e.g., a carpet pattern or design) can be expressed by a diffuse texture. The diffuse texture is reflection characteristics representing a case where the intensity of reflected light is not influenced by the incident light angle and the outgoing light angle. More specifically, in this case, reflection characteristics of an object depend on only the texture coordinate $x_o$ on a surface of the object. Therefore, a measurement condition in a case where the diffuse texture is used can be given by $(x_o)$.

<Spectrum>

In the above-mentioned exemplary embodiments, the reflection characteristics have no wavelength dependency. However, the wavelength dependency can be taken into consideration in setting a measurement condition. For example, it is useful to measure reflection characteristics for each of red, blue, and green wavelengths. Alternatively, it is useful to measure a spectrum reflectance finely in the visible light wavelength range. In this case, it is useful to set the radiance of a corresponding wavelength as the intensity of a virtual light source.

The scope of application of the present inventions is not limited to the above-mentioned exemplary embodiments. The above-mentioned exemplary embodiments can be mutually combined. For example, it is useful to combine the first exemplary embodiment and the second exemplary embodiment to simultaneously set both of measurement conditions applicable to direct reflected light and measurement conditions applicable to secondarily reflected light.

Embodiment(s) of the present inventions can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present inventions have been described with reference to exemplary embodiments, it is to be understood that the inventions are not limited to the disclosed exemplary embodiments. The scope of the following claims is to be accorded the broadest interpretation so as to encompass all such modifications and equivalent structures and functions.

This application claims the benefit of Japanese Patent Application No. 2014-074568, filed Mar. 31, 2014, which is hereby incorporated by reference herein in its entirety.

What is claimed is:

1. An information processing apparatus that determines at least one measurement condition in a real space to measure reflection characteristics of an object in the real space which is to be used to generate a virtual image of a virtual object observed from a predetermined virtual camera in a virtual space in which a virtual light source and the virtual object are disposed, wherein the virtual object reflects a texture of an object actually existing, the information processing apparatus comprising:

an information acquisition unit configured to acquire information indicating a positional relationship between the virtual light source, the virtual object, and a virtual viewpoint in the virtual space and information indicating a shape of a surface of the virtual object on which light emitted from the virtual light source is incident;

a calculation unit configured to calculate a light beam path connecting a pixel, the virtual object, and the virtual light source for each pixel of a sensor that is an imaging plane of the predetermined virtual camera before the reflection characteristics of an object are measured, based on the acquired information indicating the positional relationship and the acquired information indicating the shape; and a determination unit configured to determine at least one measurement condition among measurement conditions that can be used to measure the reflection characteristics as at least one measurement condition to be used in the reflection characteristic measurement in the real space, wherein the measurement condition indicates an object combination of a direction of incident light incident on the object and a direction of outgoing light outgoing from the object for specifying a positional relationship between a light source configured to illuminate the object in the real space and a light receiving sensor configured to capture an image of the illuminated object, wherein the determination unit determines a virtual combination of a direction of an incident light incident on the virtual object and a direction of an outgoing light outgoing from the virtual object on the light beam path in the virtual space calculated before the reflection characteristics of the object are measured, as the object combination, of the direction of the incident light incident on the object and the direction of the outgoing light outgoing from the object, to be indicated by the measurement condition, and wherein a combination excluded in the virtual combination of the direction of the incident light incident on the virtual object and the direction of the outgoing light outgoing from the virtual object on the light beam path in the virtual space calculated before the reflection characteristics of the object are measured is not regarded as the object combination, of the direction of the incident light incident on the object and the direction of the outgoing light outgoing from the object, to be indicated by the measurement condition.

2. The information processing apparatus according to claim 1, wherein the measurement conditions include information indicating a positional relationship between a light source and a light receiving sensor included in a measurement unit configured to measure reflection characteristics of the object.

3. The information processing apparatus according to claim 1, wherein the path of light is information indicating the position of the virtual light source, an incident position where the light emitted from the virtual light source reaches the virtual object, an outgoing position where the light having traveled from the virtual light source goes out from the virtual object, and the position of the virtual viewpoint.

4. The information processing apparatus according to claim 1,
wherein the information acquisition unit acquires camera data indicating characteristics of a virtual camera, light source data indicating characteristics of the virtual light source, and object data indicating characteristics of the virtual object, and
wherein the path acquisition unit acquires the path of light by calculating the path of light based on the camera data, the light source data, and the object data.

5. The information processing apparatus according to claim 4, wherein the camera data includes at least information about the position, direction, size, and number-of-pixels of an imaging plane of the virtual camera.

6. The information processing apparatus according to claim 4, wherein the light source data includes at least information indicating a type and intensity of the light source.

7. The information processing apparatus according to claim 4, wherein the object data includes at least information indicating position and shape of the virtual object.

8. The information processing apparatus according to claim 1, wherein the determination unit comprises an output unit configured to output the at least one measurement condition determined by the determination unit to a measurement unit configured to measure reflection characteristics of the object.

9. The information processing apparatus according to claim 8,
wherein the determination unit generates, as the at least one measurement condition to be output to the measurement unit, a measurement condition list including a plurality of measurement conditions, and determines, for respective measurement conditions included in the measurement condition list, a measurement order to be used in the reflection characteristic measurement, which is different from a determination order of the plurality of measurement conditions, in such a way as to reduce the measurement time compared to a case where the determination order of the plurality of measurement conditions is used as the measurement order, and
wherein the output unit outputs the measurement condition list that reflects the order to the measurement unit.

10. The information processing apparatus according to claim 1,
wherein the determination unit comprises a condition acquisition unit configured to acquire a plurality of measurement conditions based on the information indicating the positional relationship, and a comparison unit configured to compare the plurality of measurement conditions acquired by the condition acquisition unit and to identify measurement conditions that are similar to each other, and
wherein the determination unit determines at least one of the mutually similar measurement conditions that have been identified by the comparison unit as a measurement condition that is not to be used for the reflection characteristic measurement.

11. The information processing apparatus according to claim 10,
wherein the determination unit further comprises a unit configured to acquire information indicating a measurement condition already used in the measurement,
wherein the comparison unit compares the measurement condition already used in the measurement with the plurality of measurement conditions acquired by the condition acquisition unit, and
wherein the determination unit determines at least one of the plurality of measurement conditions, acquired by the condition acquisition unit and identified by the comparison unit as being similar to the measurement condition already used in the measurement, as the measurement condition that is not to be used for the reflection characteristic measurement.

12. The information processing apparatus according to claim 1, wherein the at least one measurement condition is a measurement condition to be used in a measurement of reflection characteristics of an object, and is the at least one measurement condition to be used to generate a virtual image that can be obtained when the virtual object is captured by a virtual camera from the virtual viewpoint.

13. The information processing apparatus according to claim 1, wherein a type of the reflection characteristics is at least one of bidirectional reflectance distribution function (BRDF), bidirectional scattering surface reflectance distribution function (BSSRDF), and bidirectional texture function (BTF).

14. A measurement system comprising:
an information processing apparatus; and
a measurement apparatus,
wherein the information processing apparatus determines at least one measurement condition in a real space to measure reflection characteristics of an object in the real space which is to be used to generate a virtual image of a virtual object observed from a predetermined virtual camera in a virtual space in which a virtual light source and the virtual object are disposed, wherein the virtual object reflects a texture of an object actually existing, and wherein the measurement apparatus measures reflection characteristics of an object based on the at least one measurement condition determined by the information processing apparatus,
wherein the information processing apparatus includes:
an information acquisition unit configured to acquire information indicating a positional relationship between the virtual light source, the virtual object, and a virtual viewpoint in the virtual space and information indicating a shape of a surface of the virtual object on which light emitted from the virtual light source is incident,
a calculation unit configured to calculate a light beam path connecting a pixel, the virtual object, and the virtual light source for each pixel of a sensor that is an imaging plane of the predetermined virtual camera before the reflection characteristics of an object are measured, based on the acquired information indicating the positional relationship and the acquired information indicating the shape, and a determination unit configured to determine at least one measurement condition among measurement conditions that can be used to measure the reflection characteristics as at least one measurement condition to be used in the reflection characteristic measurement in the real space, wherein the measurement condition indicates an object combination of a direction of incident light incident on the object and a direction of outgoing light outgoing from the object for specifying a positional relationship between a light source configured to illuminate the object in the real space and a light receiving sensor configured to capture an image of the illuminated object, wherein the determination unit determines a virtual combination of a direction of an incident light incident on the virtual object and a direction of an outgoing light outgoing from the virtual object on the light beam path in the virtual space calculated before the reflection characteristics of the object are measured, as the object combination, of the direction of the incident light incident on the object and the direction of the outgoing light outgoing from the object, to be indicated by the measurement condition, and wherein a combination excluded in the virtual combination of the direction of the incident light incident on the virtual object and the direction of the outgoing light outgoing from the virtual object on the light beam path in the virtual space calculated before the reflection characteristics of the object are measured is not regarded as the object combination, of the direction of the incident light incident on the object and the direction of the outgoing light outgoing from the object, to be indicated by the measurement condition, and wherein the measurement apparatus includes a measurement unit configured to measure reflection characteristics of the object based on the at least one measurement condition determined by the determination unit.

15. An information processing method for an information processing apparatus that determines at least one measurement condition in a real space to measure reflection characteristics of an object in the real space which is to be used to generate a virtual image of a virtual object observed from a predetermined virtual camera in a virtual space in which a virtual light source and the virtual object are disposed, wherein the virtual object reflects a texture of an object actually existing, the information processing method comprising:

acquiring information indicating a positional relationship between the virtual light source, the virtual object, and a virtual viewpoint in the virtual space and information indicating a shape of a surface of the virtual object on which light emitted from the virtual light source is incident;

calculating a light beam path connecting a pixel, the virtual object, and the virtual light source for each pixel of a sensor that is an imaging plane of the predetermined virtual camera before the reflection characteristics of an object are measured, based on the acquired information indicating the positional relationship and the acquired information indicating the shape; and determining at least one measurement condition among measurement conditions that can be used to measure the reflection characteristics as at least one measurement condition to be used in the reflection characteristic measurement in the real space, wherein the measurement condition indicates an object combination of a direction of incident light incident on the object and a direction of outgoing light outgoing from the object for specifying a positional relationship between a light source configured to illuminate the object in the real space and a light receiving sensor configured to capture an image of the illuminated object, wherein determining includes determining a virtual combination of a direction of an incident light incident on the virtual object and a direction of an outgoing light outgoing from the virtual object on the light beam path in the virtual space calculated before the reflection characteristics of the object are measured, as the object combination, of the direction of the incident light incident on the object and the direction of the outgoing light outgoing from the object, to be indicated by the measurement condition, and wherein a combination excluded in the virtual combination of the direction of the incident light incident on the virtual object and the direction of the outgoing light outgoing from the virtual object on the light beam path in the virtual space calculated before the reflection characteristics of the object are measured is not regarded as the object combination, of the direction of the incident light incident on the object and the direction of the outgoing light outgoing from the object, to be indicated by the measurement condition.

16. A non-transitory computer-readable medium storing a program causing a computer to execute the information processing method according to claim 15.

* * * * *